United States Patent
Bot et al.

(10) Patent No.: US 6,204,250 B1
(45) Date of Patent: *Mar. 20, 2001

(54) IMMUNIZATION OF INFANTS

(75) Inventors: Adrian Bot; Constantin Bona, both of New York, NY (US)

(73) Assignee: The Mount Sinai Medical Center of the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/755,034

(22) Filed: Nov. 22, 1996

(51) Int. Cl.⁷ .......................... A61K 31/70; C12P 21/06; C12N 5/00
(52) U.S. Cl. .......................... 514/44; 435/69.1; 435/375
(58) Field of Search .......................... 514/44; 435/172.3, 435/69.1, 375

(56) References Cited

U.S. PATENT DOCUMENTS 5,589,466   12/1996   Felgner et al. .......................... 514/44

FOREIGN PATENT DOCUMENTS 9011092   10/1990   (WO) .
9421797    9/1994   (WO) .

OTHER PUBLICATIONS

Orkin et al. "Report and Recommendations of the Panel to Assess the NIH Investment in Research on Gene Therapy," NIH Report and Recommendation, Dec. 7, 1995.*
Marshall, E. "Gene Therapy's Growing Pains," Science, vol. 269: 1050–1055, Aug. 25, 1995.*
Mulligan, R.C. "The Basic Science of Gene Therapy," Science, vol. 260: 926–932, May 14, 1993.*
Miller et al., "Targeted vectors for Gene Therapy," FASEB J., vol. 9: 190–199, Feb. 1995.*
Verma et al., "Gene Therapy–Promises, Problems, and Prospects," Nature, vol. 389: 239–242, Sep. 18, 1997.*
Ulmer et al., "Heterologous Protection Against Influenza by Injection of DNA Encoding a Viral Protein," Science, vol. 259: 1745–1748, Mar. 19, 1993.*
Pedroza et al., "DNA Vaccination against Persistent Viral Infection," J. of Virology, vol. 69: 2574–2582, Apr. 1995.*
Kuzu et al., "In vivo priming effect during various stages of ontogeny of an influenza A virus nucleoprotein peptide," Eur. J. Immunol., vol. 23: 1397–1400, Jun. 1993.*
Bot et al., "DNA Immunization of Newborn Mice with a Plasmid–Expressing Nucleoprotein of Influenza Virus," Viral Immunology, vol. 9: 207–210, Oct. 1996.*
Bachmann et al, Current Opinion in Immunology, vol. 6:320–326, 1994.*
Davis et al, "DNA–based immunization" Molecular and Cell Biology of Human Disease Series, vol. 5: 368–387, 1995.*
Lai et al, "Use of the hepatitis B recombinant DNA yeast vaccine (H–B–Vax II) in children: two doses vs three doses of 5 micrograms regime; an interim report," J. of Infection, vol. 13, Suppl. A: 19–25, Jul. 1986.*
Lai et al. "Five–year follow–up of a prospective randomized trial of hepatitis B recombinant DNA yeast vaccine vs plasma–derived vaccine in children: immunogenicity and anamnestic responses," Hepatology, vol. 18: 763–767, Oct. 1993.*
Assateerawatt et al. "Immunogenicity and efficacy of a recombinant DNA hepatitis B vaccine, GenHevac B Pasteur in high risk neonates, school children and healthy adults," vol. 11: 85–91, Jun. 1993.*
del Canho et al. "Immunogenicity of 20 micrograms of recombinant DNA hepatitis B vaccines in healthy neonates: a comparison of three different vaccination schemes," vol. 41: 30–34, Sep. 1993.*
Bot et al., 1996, J. Virol. 70: 5668–5672.
Mor et al., 1996, J. Clin. Invest. 98: 2700–2705.
Forstuber et al., 1996, Science 271: 1728–1730.
Ridge et al., 1996, Science 271: 1723–1725.
Sarzotti et al., 1996, Science 271: 1726–1725.
Crowe, 1995, Vaccine 13: 415–421.
Donnely et al., 1995, Nature Med. 1: 583–587.
Justevicz et al., 1995, J. Virol. 19: 7712–7717.
Martins et al., 1995, J. Virol. 69: 2574–2582.
Donnelly et al., 1994, J. Immunol. Meth. 176: 145–152.
Katsumi et al., 1994, Human Gene Therap. 5: 1335–1339.
Ozaki et al., 1994, J. med Virol. 42: 47–51.
Doherty 1993, Current Opin. Pediatrics 5: 3–13.
Fynan et al., 1993, Proc. Natl. Acad. Sci USA 90: 11478–11483.
Montgomery et al., 1993, DNA and Cell Biol. 12: 777–783.
Taylor et al., 1986, Immunol. 58:417–420.
Rubinstein et al., 1982, J. Exp. Med. 156:506–521.

* cited by examiner

Primary Examiner—Scott D. Priebe
Assistant Examiner—Joseph T. Woitach

(57) ABSTRACT

The present invention relates to methods and compositions which may be used to immunize infant mammals against a target antigen, wherein an immunogeniclly effective amount of a nuclic acid encoding a relevant epitope of a desired target antigen is administered to the infant. It is based, at least in part, on the discovery that such genetic immunization of infant mammals could give rise to effective cellular and humoral immune responses against target antigens.

19 Claims, 13 Drawing Sheets

FIG.6A

FIG.6B

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 19 amino acids
       (B) TYPE: amino acid
       (C) STRANDEDNESS: single
       (D) TOPOLOGY: linear (ii) MOLECULE TYPE: peptide (iii) ORIGINAL SOURCE:
       (A) ORGANISM: Human Immunodefficiency Virus Type 1

(iv) FEATURE:
       (A) NAME/KEY:
       (B) LOCATION:  301...319
       (C) OTHER INFORMATION:  Envelope Protein gp120

(v) SEQUENCE DESCRIPTION: SEQ ID NO:1:

Arg Lys Ser Ile His Ile Gly Pro Gly Arg Ala Phe Tyr Thr Thr Gly
 1               5                  10                  15

Glu Ile Ile (2) INFORMATION FOR SEQ ID NO:2:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (iii) ORIGINAL SOURCE:
       (A) ORGANISM: Influenza Virus (iv) FEATURE:
       (A) NAME/KEY:
       (B) LOCATION:
       (C) OTHER INFORMATION:  HA1 hemagglutinin protein (xi) SEQUENCE DESCRIPTION: SEQ ID NO:2:

Trp Leu Thr Lys Lys Gly Asp Ser Tyr Pro
 1               5                  10

(2) INFORMATION FOR SEQ ID NO:3:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (iii) ORIGINAL SOURCE:
       (A) ORGANISM: Influenza Virus (iv) FEATURE:
       (A) NAME/KEY:
       (B) LOCATION:
       (C) OTHER INFORMATION:  H3 protein (xi) SEQUENCE DESCRIPTION: SEQ ID NO:3:

Trp Leu Thr Lys Ser Gly Ser Thr Tyr Pro

```
        1               5                   10
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) ORIGINAL SOURCE:
        (A) ORGANISM: Influenza Virus (iv) FEATURE:
        (A) NAME/KEY:
        (B) LOCATION:
        (C) OTHER INFORMATION: H2 protein (xi) SEQUENCE DESCRIPTION: SEQ ID NO:4:

```
Trp Leu Thr Lys Glu Gly Ser Asp Tyr Pro
 1               5                   10
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) ORIGINAL SOURCE:
        (A) ORGANISM: Measles Virus (iv) FEATURE:
        (A) NAME/KEY:
        (B) LOCATION: 404...414
        (C) OTHER INFORMATION: F protein (xi) SEQUENCE DESCRIPTION: SEQ ID NO:5:

```
Ile Asn Gln Asp Pro Asp Lys Ile Leu Thr Tyr
 1               5                   10
```

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) ORIGINAL SOURCE:
        (A) ORGANISM: Foot and Mouth Disease Virus (iv) FEATURE:
        (A) NAME/KEY:
        (B) LOCATION: 141...160
        (C) OTHER INFORMATION: VP1 protein (xi) SEQUENCE DESCRIPTION: SEQ ID NO:6:

```
Met Asn Ser Ala Pro Asn Leu Arg Gly Asp Leu Gln Lys Val Ala Arg
 1               5                   10                  15
Thr Leu Pro
```

(2) INFORMATION FOR SEQ ID NO:7:

-continued

```
     (i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (iii) ORIGINAL SOURCE:
          (A) ORGANISM: Influenza PR8A Virus (iv) FEATURE:
          (A) NAME/KEY:
          (B) LOCATION:  110...120
          (C) OTHER INFORMATION:  Hemagglutinin Protein (xi) SEQUENCE DESCRIPTION: SEQ ID NO:7:

Ser Phe Glu Arg Phe Glu Ile Phe Pro Lys Glu
 1               5                  10

(2) INFORMATION FOR SEQ ID NO:8:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) ORIGINAL SOURCE:
          (A) ORGANISM:

(iv) FEATURE:
          (A) NAME/KEY:
          (B) LOCATION:
          (C) OTHER INFORMATION:  Tetanus Toxoid Protein (xi) SEQUENCE DESCRIPTION: SEQ ID NO:8:

Asn Ser Val Asp Asp Ala Leu Ile Asn Ser Thr Lys Ile Tyr Ser Tyr
 1               5                  10                  15

Phe Pro Ser Val
            20

(2) INFORMATION FOR SEQ ID NO:9:

(i) SEQUENCE CHARACTERISTICS:
          (A) LENGTH: 17 amino acids
          (B) TYPE: amino acid
          (C) STRANDEDNESS: single
          (D) TOPOLOGY: linear (ii) MOLECULE TYPE: peptide (iii) ORIGINAL SOURCE:
          (A) ORGANISM:

(iv) FEATURE:
          (A) NAME/KEY:
          (B) LOCATION:
          (C) OTHER INFORMATION:  Tetanus Toxoid (xi) SEQUENCE DESCRIPTION: SEQ ID NO:9:

Pro Glu Ile Asn Gly Lys Ala Ile His Leu Val Asn Asn Glu Ser Ser
 1               5                  10                  15

Glu (2) INFORMATION FOR SEQ ID NO:10:

(i) SEQUENCE CHARACTERISTICS:
          (A) LENGTH: 15 amino acids
```

```
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM:

(iv) FEATURE:
            (A) NAME/KEY:
            (B) LOCATION: 88...103
            (C) OTHER INFORMATION: Cytochrome C Protein (xi) SEQUENCE DESCRIPTION: SEQ ID NO:10:

Ala Asn Glu Arg Ala Asp Leu Ile Ala Tyr Leu Gln Ala Thr Lys
1               5                  10                  15

(2) INFORMATION FOR SEQ ID NO:11:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Mycobacteria (iv) FEATURE:
            (A) NAME/KEY:
            (B) LOCATION:  350...369
            (C) OTHER INFORMATION:  Heat Shock Protein (xi) SEQUENCE DESCRIPTION: SEQ ID NO:11:

Asp Gln Val His Phe Gln Pro Leu Pro Pro Ala Val Val Lys Leu Ser
1               5                  10                  15

Asp Ala Leu Ile
            20

(2) INFORMATION FOR SEQ ID NO:12:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Hen (iv) FEATURE:
            (A) NAME/KEY:
            (B) LOCATION:  48...61
            (C) OTHER INFORMATION:  Egg White Lysozyme (xi) SEQUENCE DESCRIPTION: SEQ ID NO:12:

Asp Gly Ser Thr Asp Tyr Gly Ile Leu Gln Ile Asn Ser Arg
1               5                  10

(2) INFORMATION FOR SEQ ID NO:13:

(i) SEQUENCE CHARACTERISTICS:
            (A) LENGTH: 12 amino acids
            (B) TYPE: amino acid
            (C) STRANDEDNESS: single
            (D) TOPOLOGY: linear
```

```
        (ii) MOLECULE TYPE: peptide (iii) ORIGINAL SOURCE:
             (A) ORGANISM: Streptococcus A (iv) FEATURE:
             (A) NAME/KEY:
             (B) LOCATION:  308...319
             (C) OTHER INFORMATION:  M Protein (xi) SEQUENCE DESCRIPTION: SEQ ID NO:13:

Gln Val Glu Lys Ala Leu Glu Glu Ala Asn Ser Lys
1               5                  10

(2) INFORMATION FOR SEQ ID NO:14:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) ORIGINAL SOURCE:
             (A) ORGANISM: Staphylococcus sp.

(iv) FEATURE:
             (A) NAME/KEY:
             (B) LOCATION:  81...100
             (C) OTHER INFORMATION:  Nuclease Protein (xi) SEQUENCE DESCRIPTION: SEQ ID NO:14:

Arg Thr Asp Lys Tyr Gly Arg Gly Leu Ala Tyr Ile Tyr Ala Asp Gly
1               5                   10                  15

Lys Met Val Asn
            20

(2) INFORMATION FOR SEQ ID NO:15:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (iii) ORIGINAL SOURCE:
             (A) ORGANISM: Influenza PR8A Virus (iv) FEATURE:
             (A) NAME/KEY:
             (B) LOCATION:  147...161
             (C) OTHER INFORMATION:  NP Protein (xi) SEQUENCE DESCRIPTION: SEQ ID NO:15:

Thr Tyr Gln Arg Thr Arg Ala Leu Val Arg Thr Gly Met Asp Pro
1               5                   10                  15

(2) INFORMATION FOR SEQ ID NO:16:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: protein (iii) ORIGINAL SOURCE:
             (A) ORGANISM: Influenza Virus
```

-continued (iv) FEATURE:
(A) NAME/KEY:
(B) LOCATION: 365-379
(C) OTHER INFORMATION: NP protein (xi) SEQUENCE DESCRIPTION: SEQ ID NO:16:

```
Ile Ala Ser Asn Glu Asn Met Asp Ala Met Glu Ser Ser Thr Leu
 1              5                   10                  15
```

(2) INFORMATION FOR SEQ ID NO:17:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: protein (iii) ORIGINAL SOURCE:
(A) ORGANISM:

(iv) FEATURE:
(A) NAME/KEY:
(B) LOCATION: 33-41
(C) OTHER INFORMATION: LSMV peptide (xi) SEQUENCE DESCRIPTION: SEQ ID NO:17:

```
Lys Ala Val Tyr Asn Phe Ala Thr Met
 1              5
```

(2) INFORMATION FOR SEQ ID NO:18:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: protein (iii) ORIGINAL SOURCE:
(A) ORGANISM:

(iv) FEATURE:
(A) NAME/KEY:
(B) LOCATION: 257-264
(C) OTHER INFORMATION: ovalbumin (xi) SEQUENCE DESCRIPTION: SEQ ID NO:18:

```
Ser Ile Ile Asn Phe Glu Lys Leu
 1              5
```

(2) INFORMATION FOR SEQ ID NO:19:

(i) SEQUENCE CHARACTERISTICS:
(A) LENGTH: 30 bases
(B) TYPE: nucleic acid
(C) STRANDEDNESS: single
(D) TOPOLOGY: linear (ii) MOLECULE TYPE: cDNA (iii) ORIGINAL SOURCE:
(A) ORGANISM:

(iv) FEATURE:
(A) NAME/KEY:
(B) LOCATION:
(C) OTHER INFORMATION: primer (xi) SEQUENCE DESCRIPTION: SEQ ID NO:19:

```
                                    -continued

CATTGTCTAG AATTTGAACT CCTCTAGTGG                                          30

(2) INFORMATION FOR SEQ ID NO:20:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: cDNA (iii) ORIGINAL SOURCE:
        (A) ORGANISM:

(iv) FEATURE:
        (A) NAME/KEY:
        (B) LOCATION:
        (C) OTHER INFORMATION:   primer (xi) SEQUENCE DESCRIPTION: SEQ ID NO:20:

AATTTGAATG ATGCAAC                                                        17
```

IMMUNIZATION OF INFANTS

SPECIFICATION

Figure 1A:
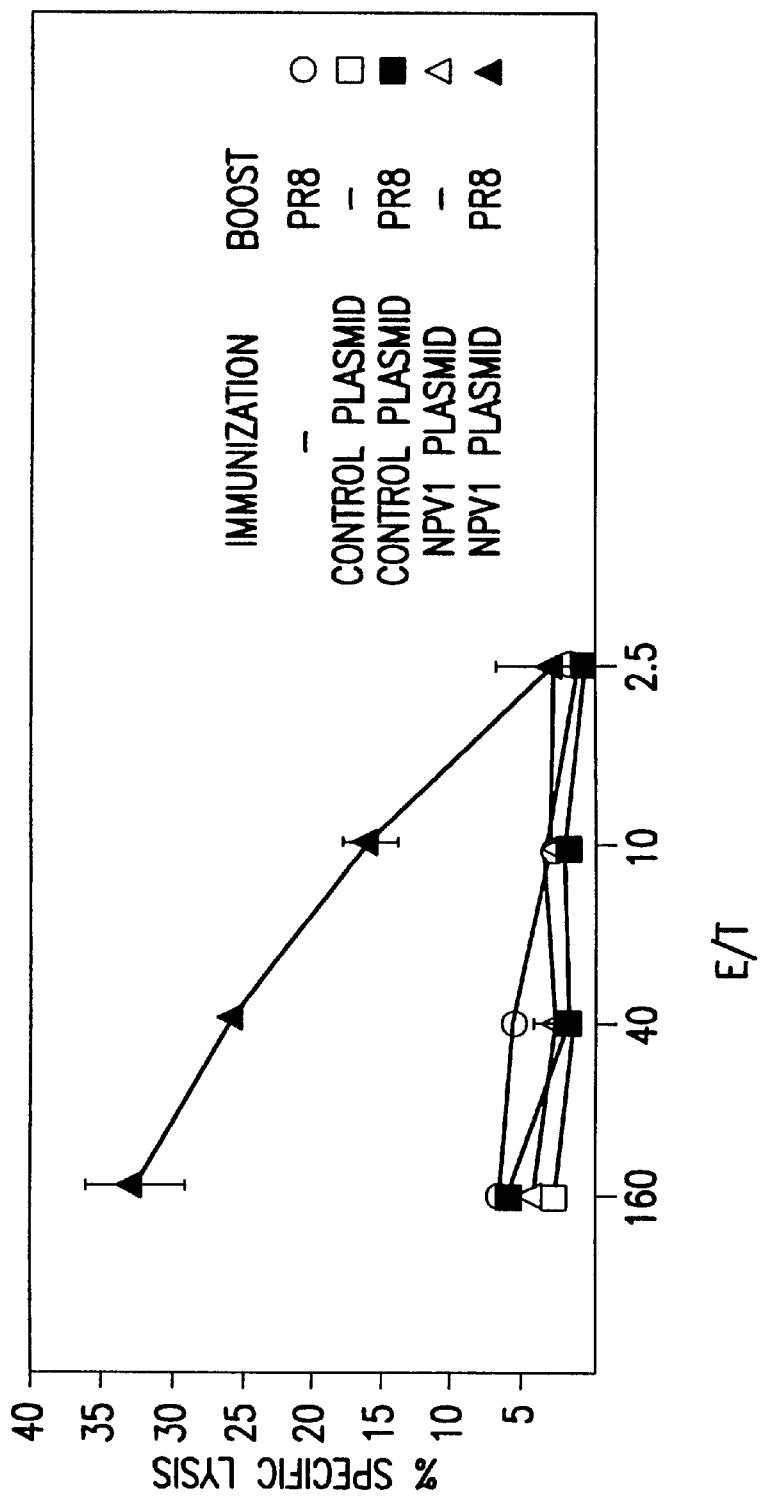
Figure 1B:
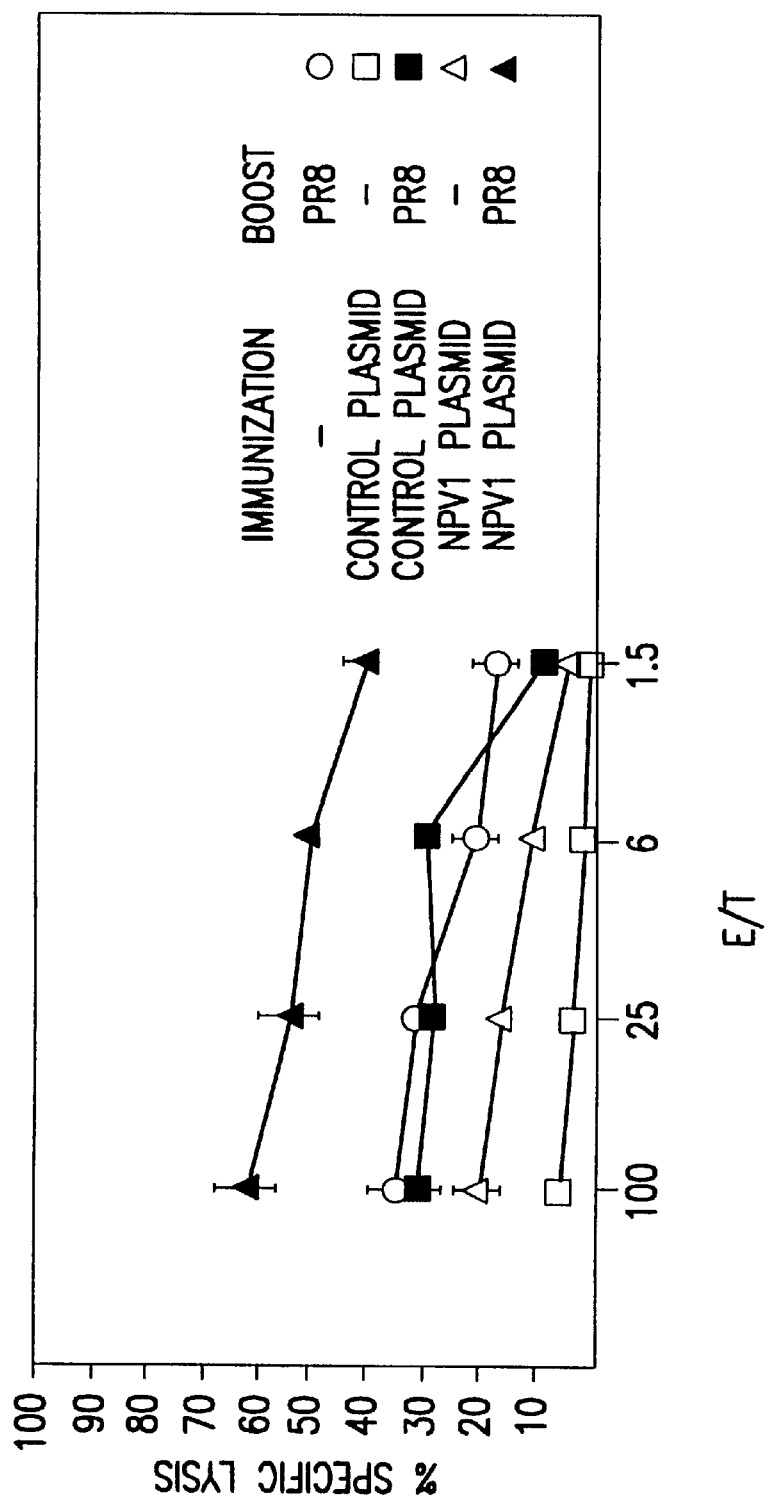
Figure 1C:
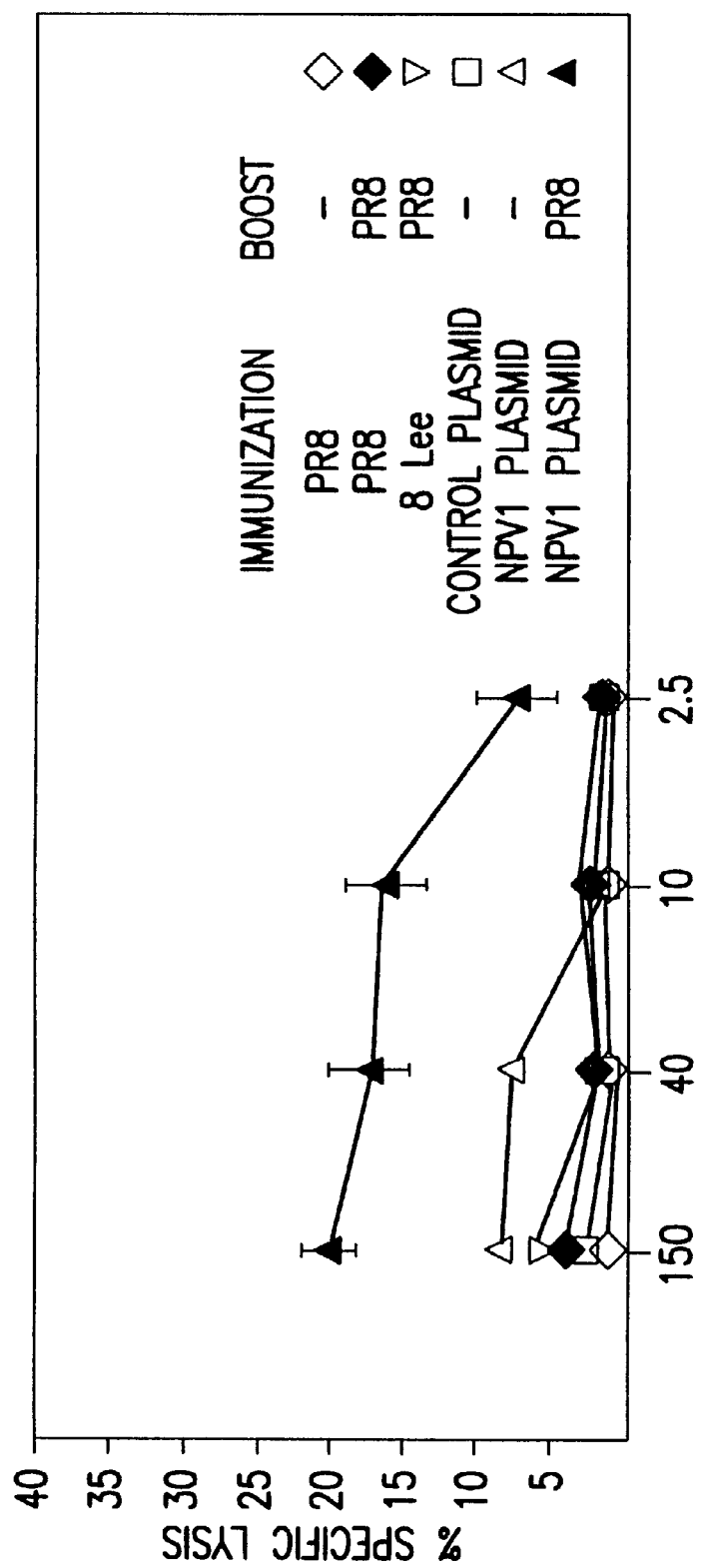
Figure 1D:
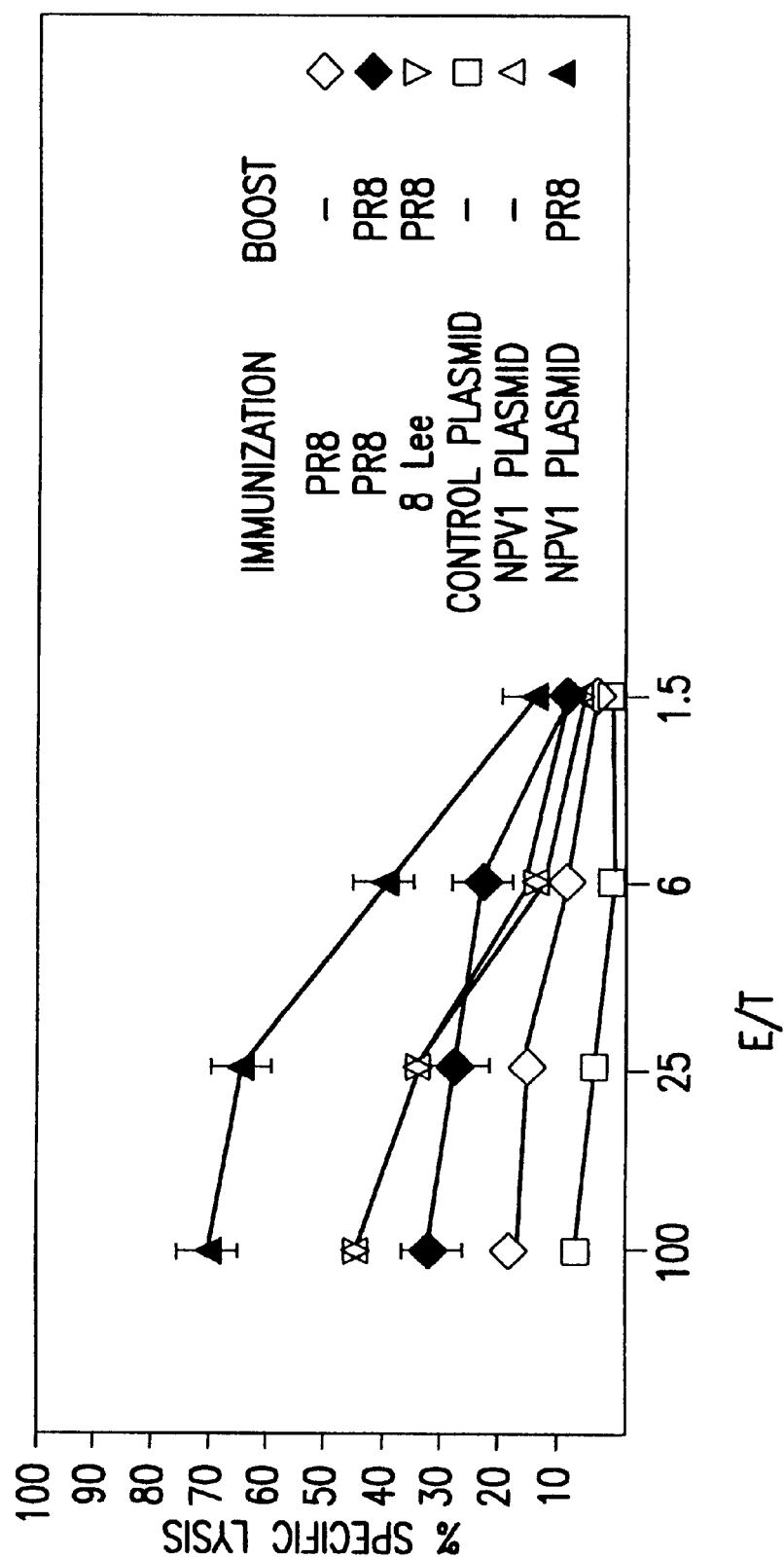

The invention contained herein was funded, at least in part, by NIH-NIAID grant No. GCO #87-009 MI, so that the United States Government holds certain rights herein.

1. INTRODUCTION

The present invention relates to methods and compositions which may be used to immunize infant mammals against a target antigen, wherein an immunogenically effective amount of a nucleic acid encoding a relevant epitope of a desired target antigen is administered to the infant.

2. BACKGROUND OF THE INVENTION

A properly operating immune system enables an organism to maintain a healthy status quo by distinguishing between antigens associated with the organism itself, which are allowed to persist, and antigens associated with disease, which are disposed of. Decades ago, Burnet proposed that the immune system's ability to distinguish between "self" and "non-self" antigens results from the elimination of self-reactive lymphocytes in the developing organism (Burnet, 1959, *The Clonal Selection Theory of Acquired Immunity*, Vanderbilt Univ. Press, Nashville, Tenn.). The phenomenon wherein an organism loses the ability to produce an immune response toward an antigen is referred to as "tolerance".

Over the years, a number of observations consistent with the clonal selection theory of tolerance have been documented. For example, genetically non-identical twin cattle, which share a placenta and are exposed to each other's blood cells in utero, fail to reject the allogeneic cells of their sibling as adults (Owen, 1945, Science 102:400). As another example, adult rodents that had been injected, at birth, with hemopoietic cells from a genetically distinct donor rodent strain were able to accept tissue transplants from that donor strain (Billingham et al., 1953, Nature 172:603; Billingham, 1956, Proc. R. Soc. London Ser. B. 239:44). However, in the early 1980's it was shown that the injection of minute amounts of antigen (namely an immunoglobulin expressing A48 regulatory idiotype) induced the expansion of helper T cells (Rubinstein et al., 1982, J. Exp. Med. 156:506–521).

The concept of tolerization is associated with the traditional belief that neonates are themselves incapable of mounting an effective immune response. It has been generally believed that neonates rely on maternal antibodies (passively transferred via the placenta) for immunity, until the neonate begins to synthesize its own IgG anti-bodies (at about 3–4 months after birth, in humans; Benjamini and Leskowitz, 1988, "Immunology, A Short Course", Alan R. Liss, Inc., New York, p. 65). In spite of the fact that passive immunity still plays a dominant role until 6–8 months after birth, the immune system gradually acquires the ability to mount adult-like immune responses.

More recently, several groups have reported findings that dispute the hypothesis that exposure to an antigen in early life disarms the ability of the immune system to react to that antigen.

Forsthuber et al. (1996, Science 271:1728–1730; "Forsthuber") suggest that the impaired lymph node response of so-called "tolerized" mice was an artifact caused by a technical inability to assess immune function. They reported that neonatal mice, injected with hen egg lysozyme (HEL) in Freund's incomplete adjuvant ("IFA") according to a protocol considered to induce tolerance in adults as well as neonates, displayed an impaired response in the lymph nodes consistent with tolerization. However, the spleen cells of these mice reportedly proliferated vigorously in response to HEL, a response previously unmeasurable due to technical limitations. The authors propose that neonatal injection did not tolerize, but rather induced functional memory cells that were detectable in spleen but not lymph nodes.

Sarzotti et al. (1996, Science 271:1726; "Sarzotti") report that inoculation of newborn mice with a high dose of Cas-Br-M murine leukemia virus ("Cas") does not result in immunological unresponsiveness, but rather leads to a non-productive type 2 response which is likely to have a negative effect on the induction of mature effector cells. According to Sarzotti, clonal deletion of relevant CTL was not observed in mice infected at birth with a low dose of Cas.

Finally, Ridge et al. (1996, Science 271:1723–1726; "Ridge") proposes that previous reports of tolerance induction may have been associated with a relative paucity of antigen presenting cells. Ridge observed the induction of CTL reactivity in neonatal mice injected with antigen expressed on dendritic cells (which are so-called professional antigen presenting cells).

The use of nucleic acids as vaccines was known prior to the present invention (see, for example, International Application Publication No. WO 94/21797, by Merck & Co. and Vical, Inc., and International Application Publication No. WO 90/11092). It was not known, however, that such vaccines could be used to induce an immune response, including humoral and cellular components, in infant mammals.

3. SUMMARY OF THE INVENTION

The present invention relates to methods and compositions which may be used to immunize infant mammals against a target antigen, wherein an immunogenically effective amount of a nucleic acid encoding a relevant epitope of a desired target antigen is administered to the infant. It is based, at least in part, on the discovery that such genetic immunization of infant mammals could give rise to effective cellular (including the induction of cytotoxic T lymphocytes) and humoral immune responses against target antigen. Moreover, the present invention may reduce the need for subsequent boost administrations (as are generally required for protein and killed pathogen vaccines), and may prevent side-effects associated with live attenuated vaccines. For instance, the World Health Organization recommends waiting nine months after birth before immunizing against rubella, measles, and mumps, in order to avoid undesirable side effects associated with vaccination against these diseases. Similarly, the World Health Organization recommends waiting two months after birth before immunizing children against influenza virus. In addition to concern over side effects, there is doubt as to whether an effective immune response may be generated using these conventional vaccines prior to the recommended ages.

4. DESCRIPTION OF THE FIGURES

FIGS. 1A–F. Primary and secondary NP-specific cytotoxicity one month after injection of newborn (D–F) or adult (A–C) mice with DNA encoding influenza nucleoprotein (NPV1). The percentage of specific lysis was determined in a standard 4-hour $^{51}$Cr release assay for CTL (cytotoxic T lymphocytes) obtained from newborn or adult animals immunized with NPV1 or control DNA and boosted (or not) with live PR8 virus one month after completing the immunization. An additional control group was injected with saline and boosted one month later with virus. Spleen cells were harvested 7 days after boosting and the percentage of NP-specific cytotoxicity was determined immediately (i.e., primary cytotoxicity) or after incubation for five days with irradiated spleen cells, NP peptide, and IL-2 (i.e., secondary cytotoxicity) as described in Zaghouani et al., 1992, J. Immunol. 148:3604–3609. CTLs were assayed against P815 cells coated with NP peptide (5 µg/ml) or infected with PR8 (not shown) or B Lee virus.

Figure 2A:
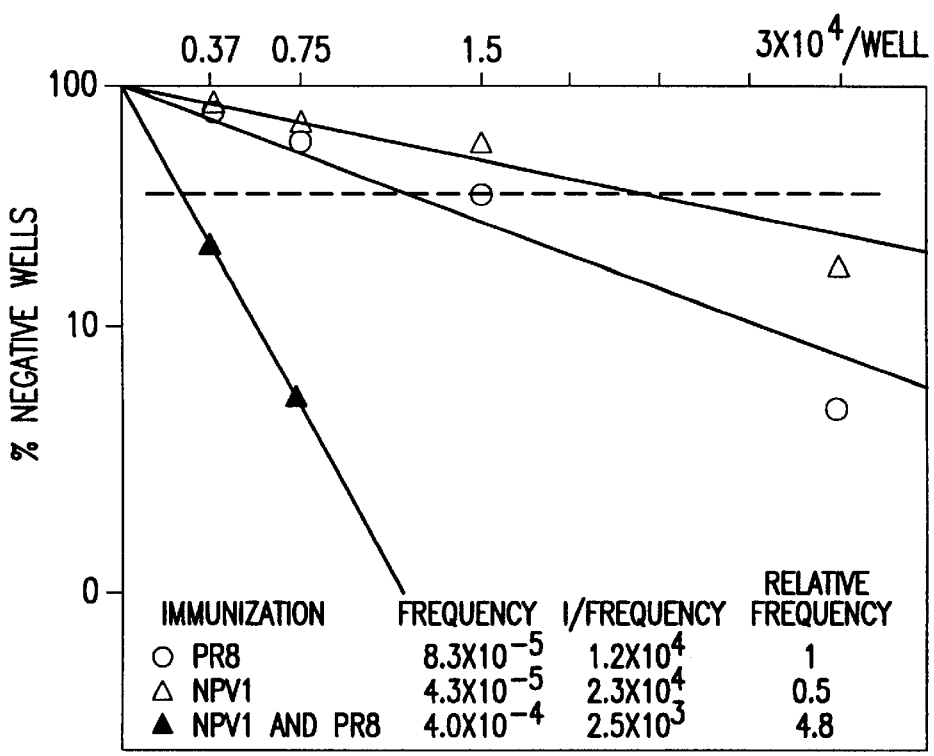
Figure 2B:
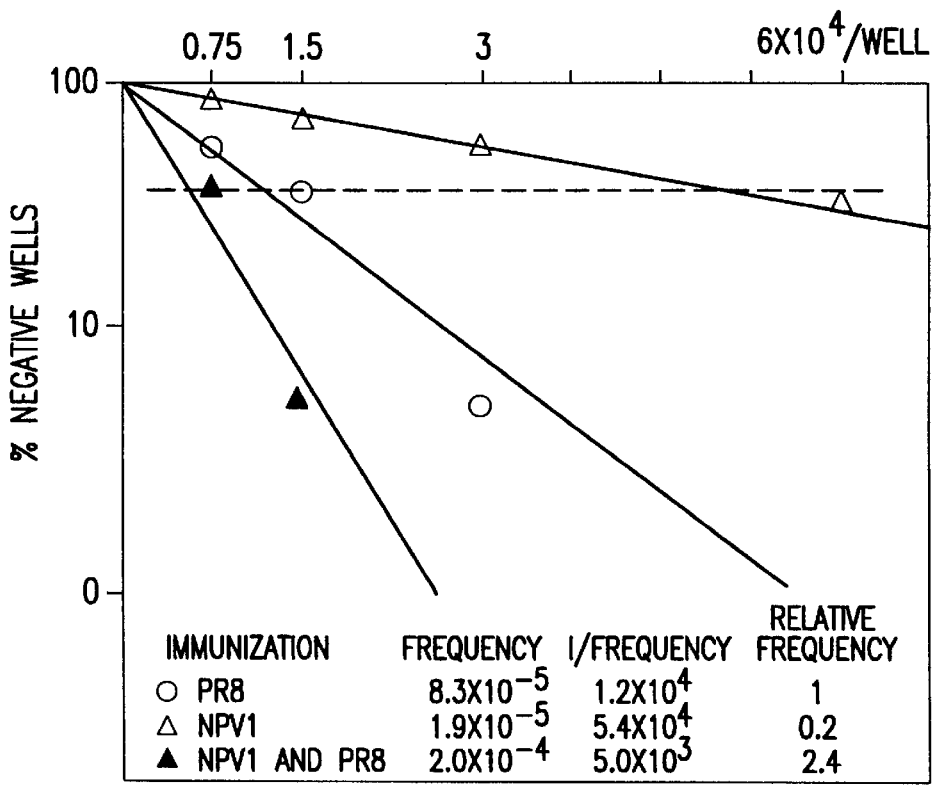

FIGS. 2A–B. Limiting dilution assay to determine the frequency of NP-specific CTL precursors one month after injection of newborn (B) and adult (A) mice with NPV1. Splenocytes harvested 7 days after PR8 boosting from newborn and adult mice vaccinated with NPV1 or control plasmid were incubated in serial dilution ($6 \times 10^4$ to $2 \times 10^1$ splenocytes/well) for 5 days with x-irradiated, PR8-infected splenocytes from non-immunized BALB/c mice in the presence of IL-2 (6 units/ml). The incubation was carried out in 96-well microtiter plates with 24 wells for each dilution of effector cells. Cytotoxicity was assessed against PR8-infected or non-infected P815 cells. Those wells exhibiting percentage lysis greater than background plus three standard deviations were regarded as positive.

Figure 3:
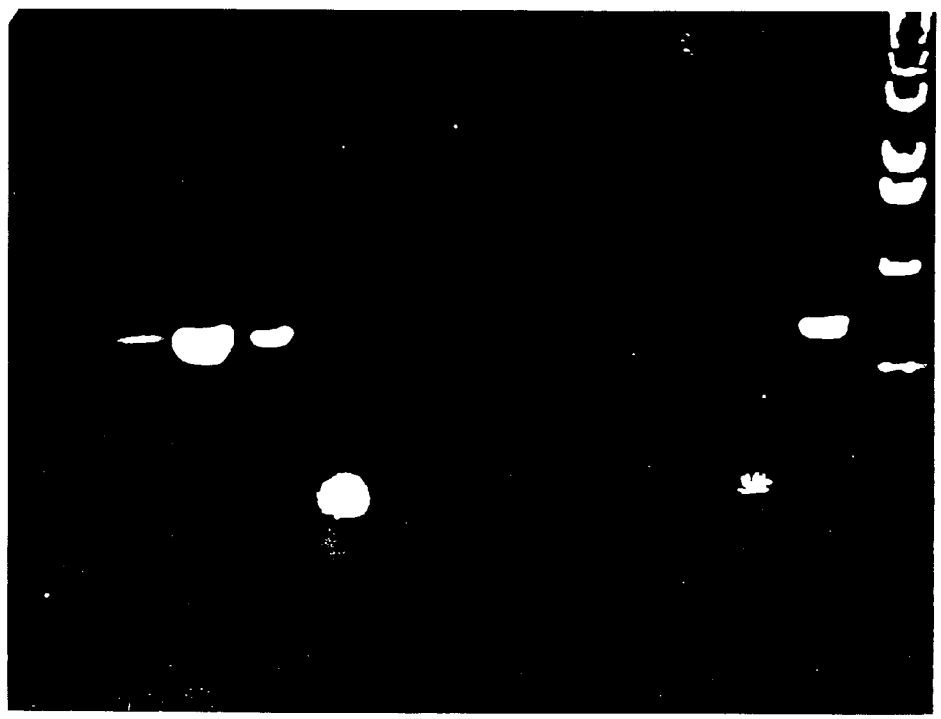

FIG. 3. Detection of DNA in muscle of BALB/c mice infected with NPV1. Muscle tissue was removed from the site of injection in the right gluteal muscle of newborns or tibial muscle of adults one month after completion of the vaccination schedule. DNA recovered from the muscle tissue on the left flank of each animal served as a control. The labeling above each lane indicates the origin of DNA.

Figure 4A:
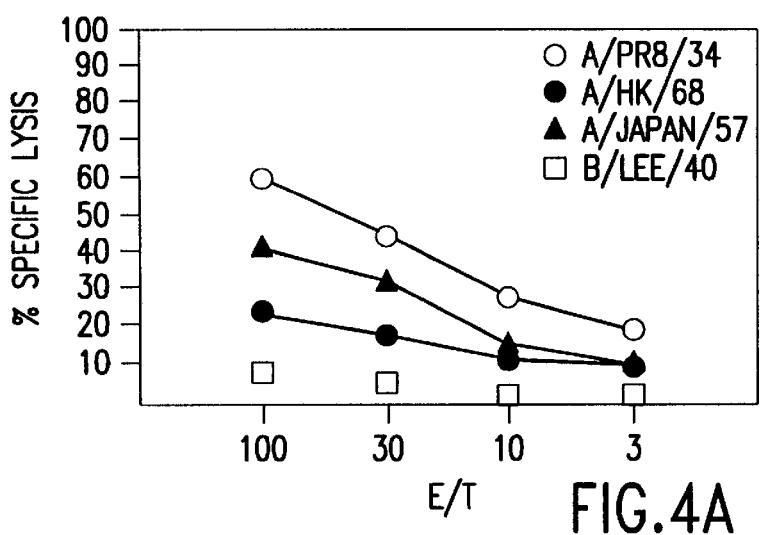
Figure 4B:
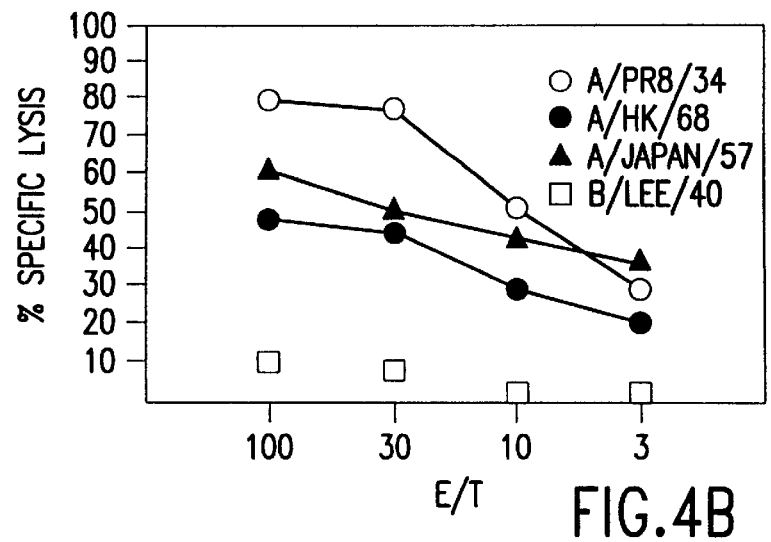
Figure 4C:
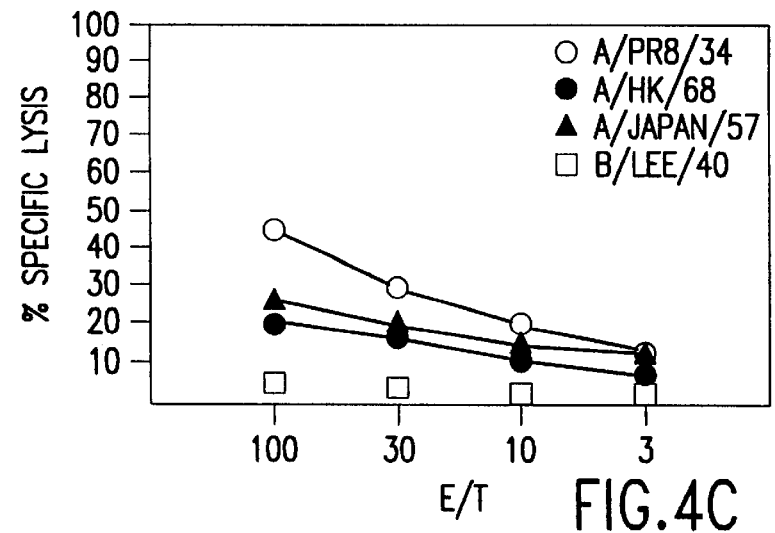
Figure 5A:
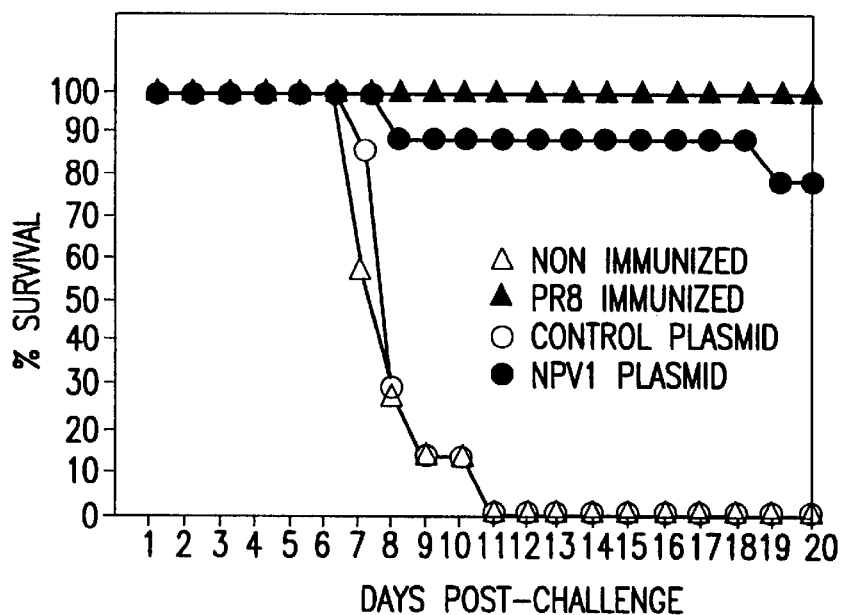
Figure 5B:
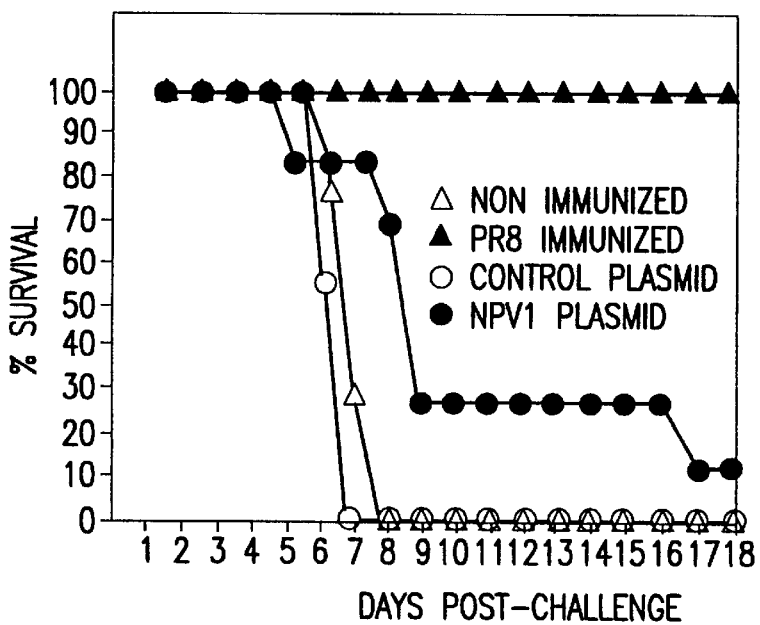
Figure 5C:
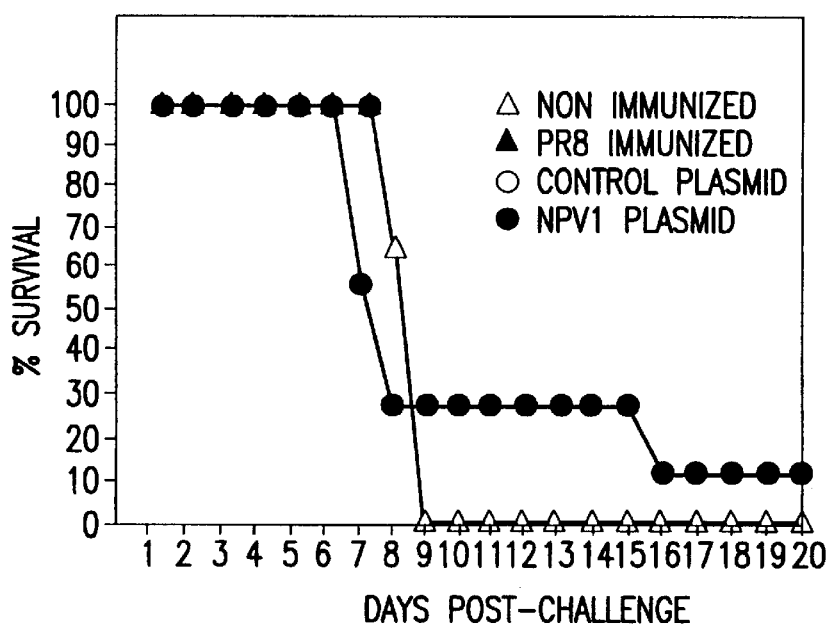
Figure 5D:
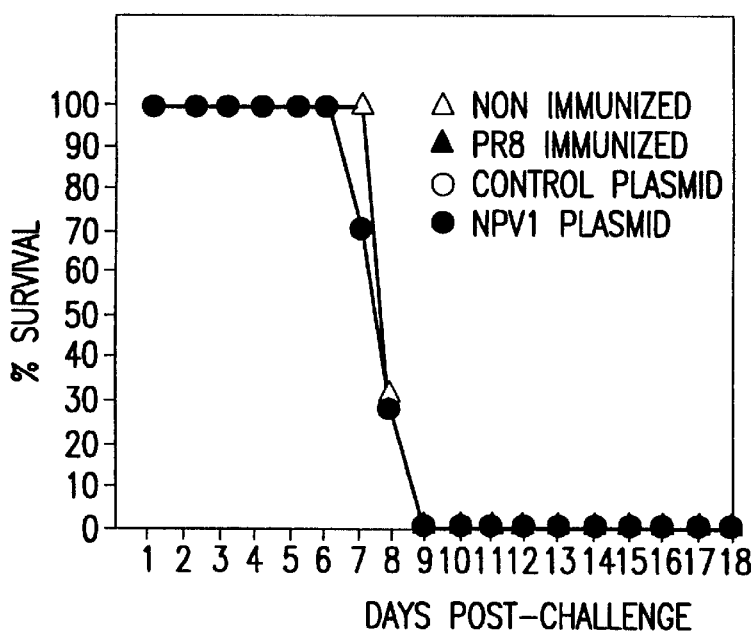
Figure 5E:
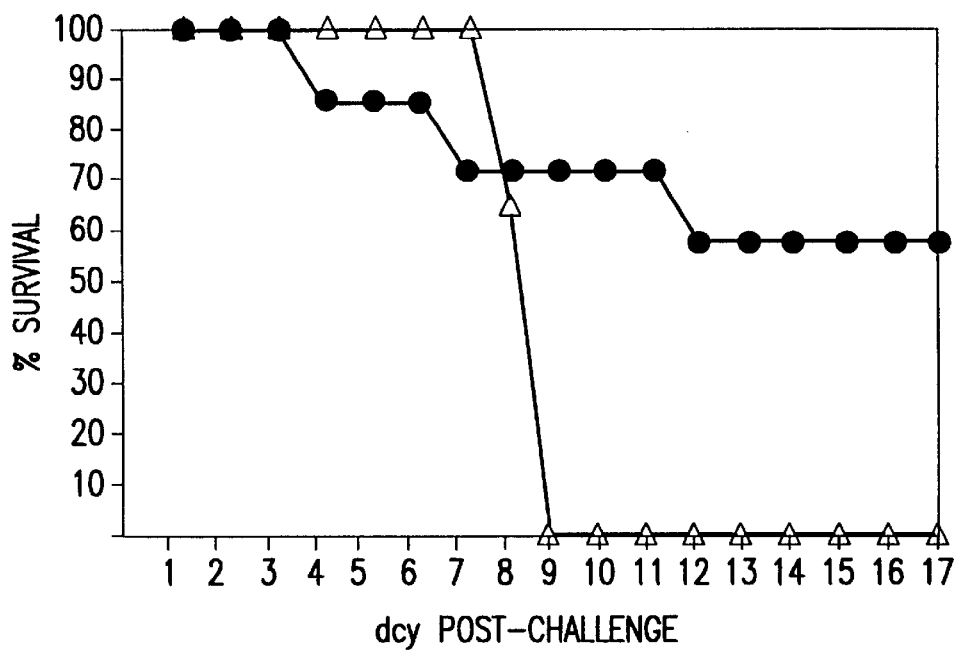
Figure 5F:
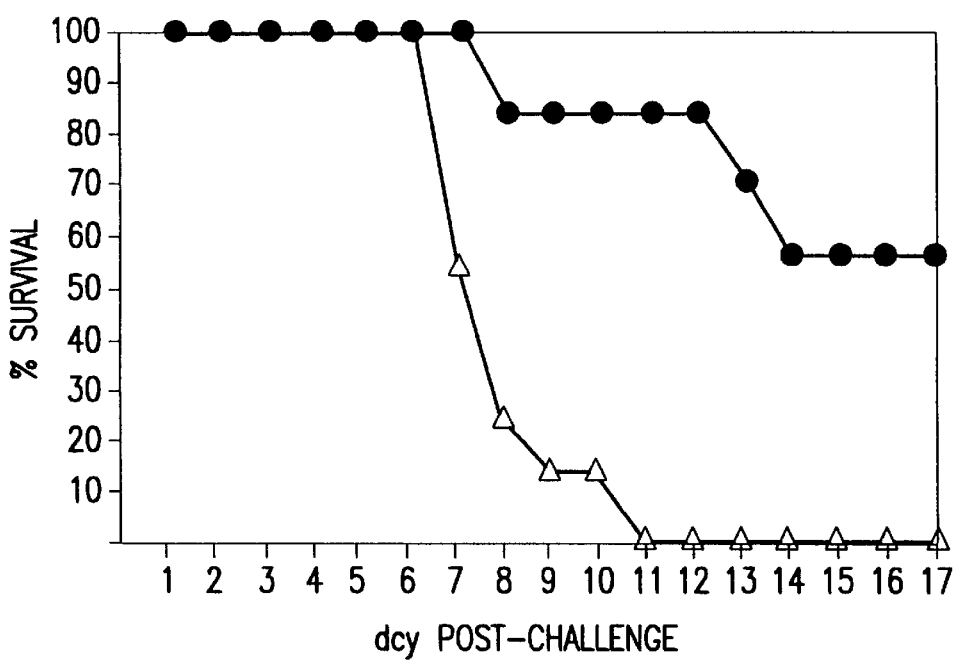
Figure 7A:
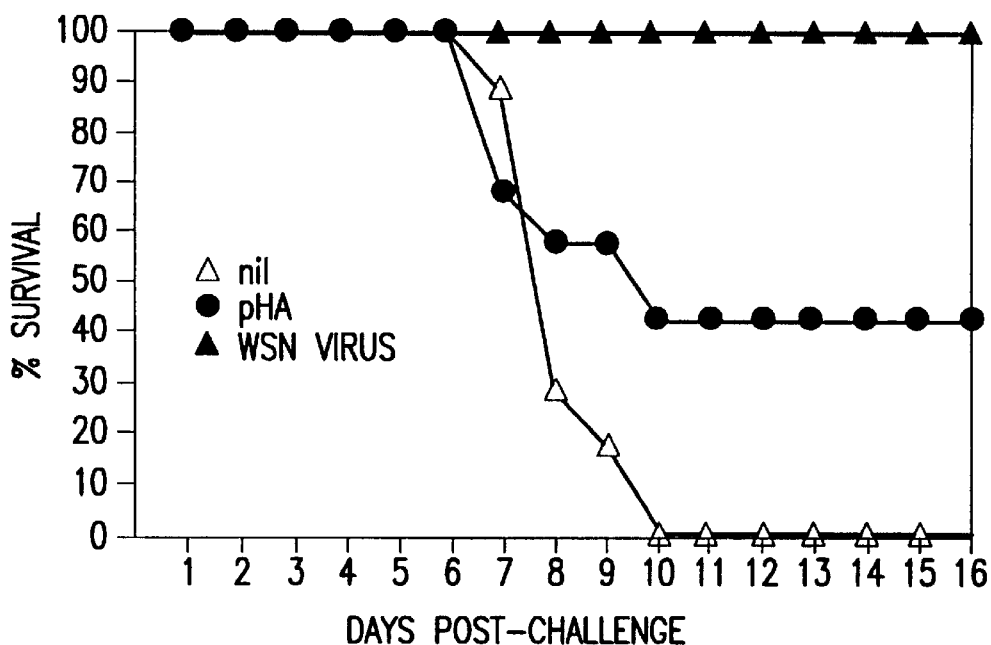
Figure 7B:
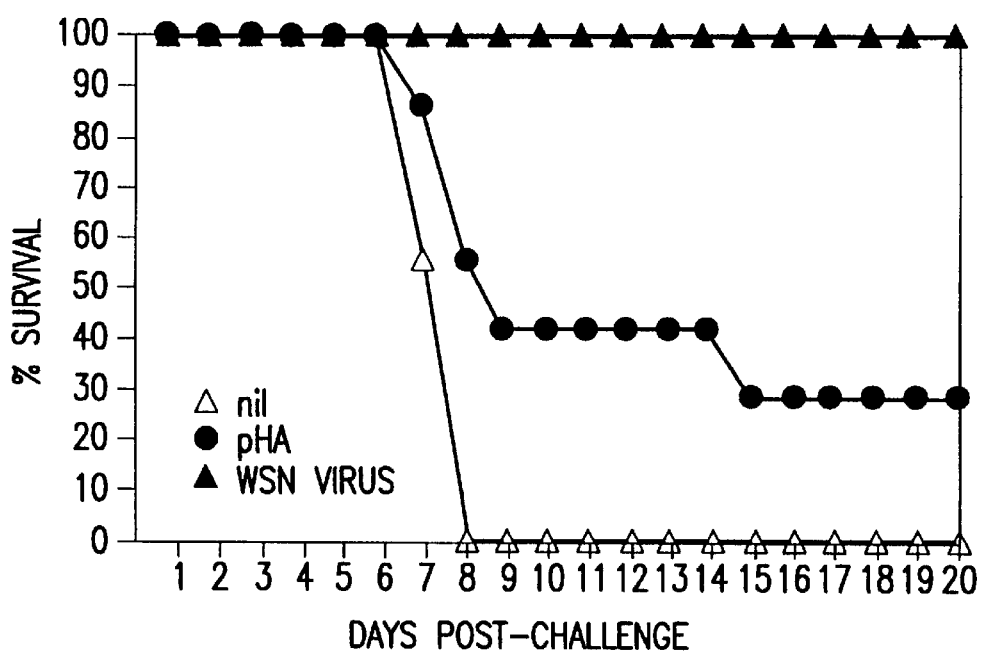
Figure 7C:
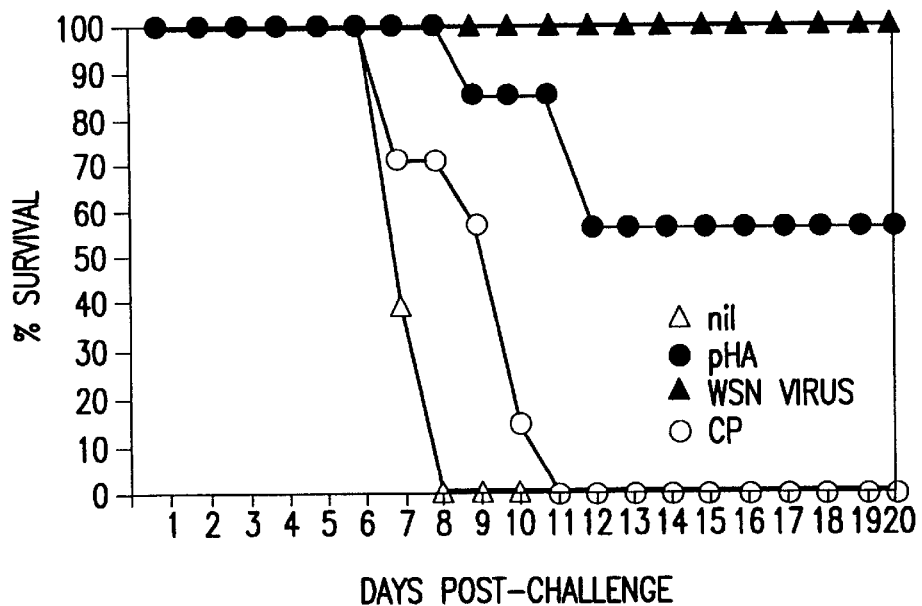
Figure 7D:
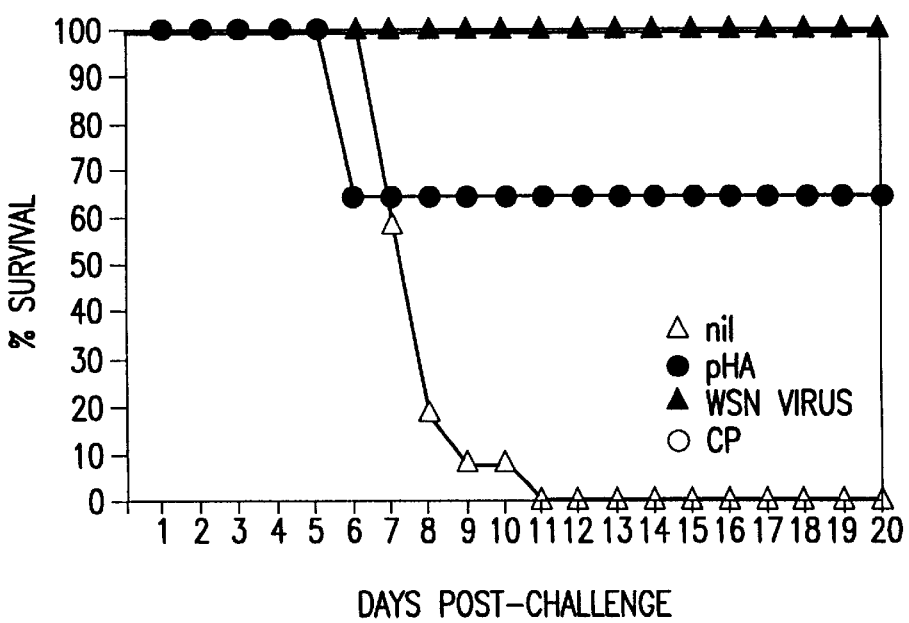

FIGS. 4 A–C. Cross-reactive CTLS generated in newborns injected with NPV1. The percentage of specific lysis was determined using a standard $^{51}$Cr release assay. Spleen cells were harvested from (A) PR8 immunized mice; (B) genetically immunized newborns that were immunized one month later with PR8 virus and (C) genetically immunized newborns Spleen cells were cultured for 4 days with irradiated PR8-infected spleen cells, then assayed in the presence of $^{51}$Cr-labeled P815 cells noninfected or infected with PR8, A/HK, A/Japan or B lee virus.

FIGS. 5A–F. Survival of genetically immunized newborn and adult mice challenged 1 mo. (A–D) or 3 mo. (E and F) after immunization with $1.5 \times 10^4$ TCID$_{50}$ PR8 virus or $3 \times 10^5$ TCID$_{50}$ HK virus via aerosol.

Figures 6A, 6B:
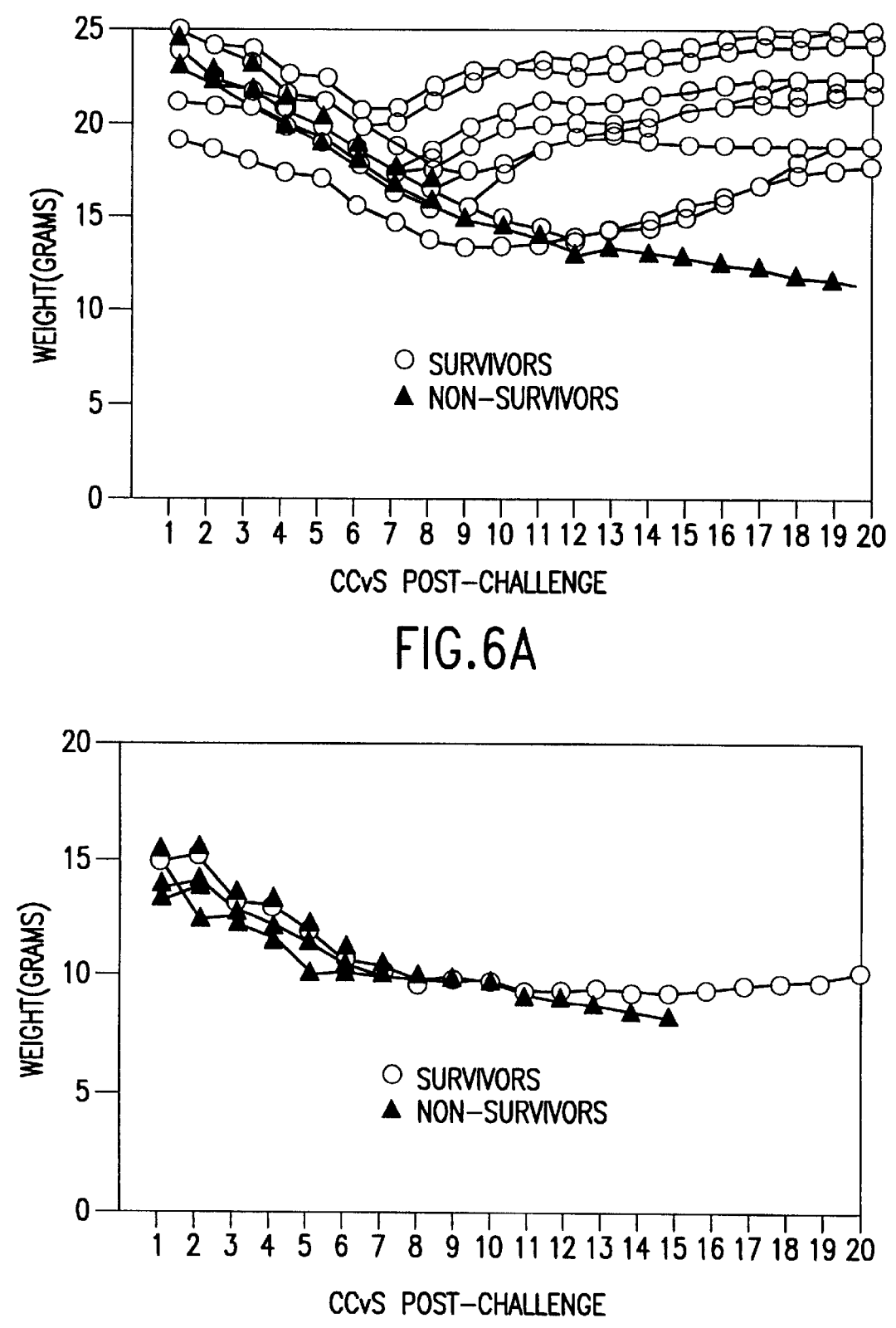

FIGS. 6A–B. Kinetics of body-weight loss and recovery in immunized adult (A) or newborn (B) mice challenged with $1.5 \times 10^4$ TCID50 PR8 virus one month after completing the immunization.

FIGS. 7A–D. Survival of (A–B) newborn and (C–D) adult mice immunized with pHA plasmid encoding hemagglutinin of WSN influenza virus and challenged with LD$_{100}$ of WSN or PR8 virus, 1 month after immunization.

5. DETAILED DESCRIPTION OF THE INVENTION

For purposes of clarity of description, and not by way of limitation, the detailed description of the invention is divided into the following subsections:

(i) compositions for immunization; and
(ii) methods of immunization.

5.1. Compositions For Immunization

The present invention provides for compositions which may be used to immunize infant mammals against a target antigen which comprise an effective amount of a nucleic acid encoding a relevant epitope of the target antigen in a pharmaceutically acceptable carrier.

Nucleic acids which may be used herein include deoxyribonucleic acid ("DNA") as well as ribonucleic acid ("RNA"). It is preferable to use DNA in view of its greater stability to degradation.

The term "target antigen" refers to an antigen toward which it is desirable to induce an immune response, Such an antigen may be comprised in a pathogen, such as a viral, bacterial, protozoan, fungal, yeast, or parasitic antigen, or may be comprised in a cell, such as a cancer cell or a cell of the immune system which mediates an autoimmune disorder. For example, but not by way of limitation, the target antigen may be comprised in an influenza virus, a cytomegalovirus, a herpes virus (including HSV-I and HSV-II), a vaccinia virus, a hepatitis virus (including but not limited to hepatitis A, B, C, or D), a varicella virus, a rotavirus, a papilloma virus, a measles virus, an Epstein Barr virus, a coxsackie virus, a polio virus, an enterovirus, an adenovirus, a retrovirus (including, but not limited to, HIV-1 or HIV-2), a respiratory syncytial virus, a rubella virus, a Streptococcus bacterium (such as *Streptococcus pneumoniae*), a Staphylococcus bacterium (such as *Staphylococcus aureus*), a Hemophilus bacterium (such as *Hemophilus influenzae*), a Listeria bacterium (such as *Listeria monocytogenes*), a Klebsiella bacterium, a Gram-negative bacillus bacterium, an Escherichia bacterium (such as *Escherichia coli*), a Salmonella bacterium (such as *Salmonella typhimurium*), a Vibrio bacterium (such as *Vibrio cholerae*), a Yersinia bacterium (such as *Yersinia pestis* or *Yersinia enterocoliticus*), an Enterococcus bacterium, a Neisseria bacterium (such as *Neiserria meningitidis*), a Corynebacterium bacterium (such as *Corynebacterium diphtheriae*), a Clostridium bacterium (such as *Clostridium tetani*), a Mycoplasma (such as *Mycoplasma pneumoniae*), a Pseudomonas bacterium, (such as *Pseudomonas aeruginosa*), a Mycobacteria bacterium (such as *Mycobacterium tuberculosis*), a Candida yeast, an Aspergillus fungus, a Mucor fungus, a toxoplasma, an amoeba, a malarial parasite, a trypanosomal parasite, a leishmanial parasite, a helminth, etc. Specific nonlimiting examples of such target antigens include hemagglutinin, nucleoprotein, M protein, F protein, HBS protein, gp120 protein of HIV, nef protein of HIV, and listeriolysine. In alternative embodiments, the target antigen may be a tumor antigen, including, but not limited to, carcinoembryonic antigen ("CEA"), melanoma associated antigens, alpha fetoprotein, papilloma virus antigens, Epstein Barr antigens, etc.

The term "relevant epitope", as used herein, refers to an epitope comprised in the target antigen which is accessible to the immune system. For example, a relevant epitope may be processed after penetration of a microbe into a cell or recognized by antibodies on the surface of the microbe or microbial proteins. Preferably, an immune response directed toward the epitope confers a beneficial effect; for example, where the target antigen is a viral protein, an immune response toward a relevant epitope of the target antigen at least partially neutralizes the infectivity or pathogenicity of the virus. Epitopes may be B-cell or T-cell epitopes.

The term “B cell epitope”, as used herein, refers to a peptide, including a peptide comprised in a larger protein, which is able to bind to an immunoglobulin receptor of a B cell and participates in the induction of antibody production by the B cells.

For example, and not by way of limitation, the hypervariable region 3 loop (“V3 loop”) of the envelope protein of human immunodeficiency virus (“HIV”) type 1 is known to be a B cell epitope. Although the sequence of this epitope varies, the following consensus sequence, corresponding to residues 301–319 of HIV-1 gp120 protein, has been obtained: Arg-Lys-Ser-Ile-His-Ile-Gly-Pro-Gly-Arg-Ala-Phe-Tyr-Thr-Thr-Gly-Glu-Ile-Ile (SEQ ID NO:1).

Other examples of known B cell epitopes which may be used according to the invention include, but are not limited to, epitopes associated with influenza virus strains, such as Trp-Leu-Thr-Lys-Lys-Gly-Asp-Ser-Tyr-Pro (SEQ ID NO:2), which has been shown to be an immunodominant B cell epitope in site B of influenza HA1 hemagglutinin, the epitope Trp-Leu-Thr-Lys-Ser-Gly-Ser-Thr-Tyr-Pro (H3; SEQ ID NO:3), and the epitope Trp-Leu-Thr-Lys-Glu-Gly-Ser-Asp-Tyr-Pro (H2; SEQ ID NO:4) (Li et al., 1992, J. Virol. 66:399–404); an epitope of F protein of measles virus (residues 404–414; Ile-Asn-Gln-Asp-Pro-Asp-Lys-Ile-Leu-Thr-Tyr SEQ ID NO:5; Parlidos et al., 1992, Eur. J. Immunol. 22:2675–2680); an epitope of hepatitis virus pre-Sl region, from residues 132–145 (Leclerc, 1991, J. Immunol. 147:3545–3552); and an epitope of foot and mouth disease VP1 protein, residues 141–160, Met-Asn-Ser-Ala-Pro-Asn-Leu-Arg-Gly-Asp-Leu-Gln-Lys-Val-Ala-Arg-Thr-Leu-Pro (SEQ ID NO:6; Clarke et al., 1987, Nature 330:381–384).

Still further B cell epitopes which may be used are known or may be identified by methods known in the art, as set forth in Caton et al., 1982, Cell 31:417–427.

In additional embodiments of the invention, peptides which may be used according to the invention may be T cell epitopes. The term “T cell epitope”, as used herein, refers to a peptide, including a peptide comprised in a larger protein, which may be associated with MHC self antigens and recognized by a T cell, thereby functionally activating the T cell.

For example, the present invention provides for $T_h$ epitopes, which, in the context of MHC class II self antigens, may be recognized by a helper T cell and thereby promote the facilitation of B cell antibody production via the $T_h$ cell.

For example, and not by way of limitation, influenza A hemagglutinin (HA) protein of PR8 strain, bears, at amino acid residues 110–120, a $T_h$ epitope having the amino acid sequence Ser-Phe-Glu-Arg-Phe-Glu-Ile-Phe-Pro-Lys-Glu (SEQ ID NO:7).

Other examples of known T cell epitopes include, but are not limited to, two promiscuous epitopes of tetanus toxoid, Asn-Ser-Val-Asp-Asp-Ala-Leu-Ile-Asn-Ser-Thr-Lys-Ile-Tyr-Ser-Tyr-Phe-Pro-Ser-Val (SEQ ID NO:8) and Pro-Glu-Ile-Asn-Gly-Lys-Ala-Ile-His-Leu-Val-Asn-Asn-Glu-Ser-Ser-Glu (SEQ ID NO:9, Ho et al., 1990, Eur. J. Immunol. 20:477–483); an epitope of cytochrome c, from residues 88–103, Ala-Asn-Glu-Arg-Ala-Asp-Leu-Ile-Ala-Tyr-Leu-Gln-Ala-Thr-Lys (SEQ ID NO:10); an epitope of Mycobacteria heatshock protein, residues 350–369, Asp-Gln-Val-His-Phe-Gln-Pro-Leu-Pro-Pro-Ala-Val-Val-Lys-Leu-Ser-Asp-Ala-Leu-Ile SEQ ID NO:11; Vordermir et al., Eur. J. Immunol. 24:2061–2067); an epitope of hen egg white lysozyme, residues 48–61, Asp-Gly-Ser-Thr-Asp-Tyr-Gly-Ile-Leu-Gln-Ile-Asn-Ser-Arg (SEQ ID NO:12; Neilson et al., 1992, Proc. Natl. Acad. Sci. U.S.A. 89:7380–7383); an epitope of Streptococcus A M protein, residues 308–319, Gln-Val-Glu-Lys-Ala-Leu-Glu-Glu-Ala-Asn-Ser-Lys (SEQ ID NO:13; Rossiter et al., 1994, Eur. J. Immunol. 24:1244–1247); and an epitope of Staphylococcus nuclease protein, residues 81–100, Arg-Thr-Asp-Lys-Tyr-Gly-Arg-Gly-Leu-Ala-Tyr-Ile-Tyr-Ala-Asp-Gly-Lys-Met-Val-Asn (SEQ ID NO:14; de Magistris, 1992, Cell 68:1–20). Still further $T_h$ epitopes which may be used are known or may be identified by methods known in the art.

As a further example, a relevant epitope may be a $T_{CTL}$ epitope, which, in the context of MHC class I self antigens, may be recognized by a cytotoxic T cell and thereby promote CTL-mediated lysis of cells comprising the target antigen. Nonlimiting examples of such epitopes include epitopes of influenza virus nucleoproteins TYQRTRALVRTGMDP (SEQ ID NO:15) or IASNENMDAMESSTL (SEQ ID NO:16) corresponding to amino acid residues 147–161 and 365–379, respectively (Taylor et al., 1989 Immunogenetics 26:267; Townsend et al., 1983, Nature 348:674); LSMV peptide, KAVYNFATM, amino acid residues 33–41 (SEQ ID NO:17); Zinhernagel et al., 1974, Nature 248:701–702); and ovalbumin peptide, SIINFEKL, corresponding to amino acid residues 257–264 (SEQ ID NO:18; Cerbone et al., 1983, J. Exp. Med. 163:603–612).

The nucleic acids of the invention encode a relevant epitope, and may optionally further comprise elements that regulate the expression and/or stability and/or immunogenicity of the relevant epitope. For example, elements that regulate the expression of the epitope include, but are not limited to, a promoter/enhancer element, a transcriptional initiation site, a polyadenylation site, a transcriptional termination site, a ribosome binding site, a translational start codon, a translational stop codon, a signal peptide, etc. Specific examples include, but are not limited to, a promoter and intron A sequence of the initial early gene of cytomegalovirus (CMV or SV40 virus (“SV40”); Montgomery et al., 1993, DNA and Cell Biology 12:777–783). With regard to enhanced stability and/or immunogenicity of the relevant epitope, it may be desirable to comprise the epitope in a larger peptide or protein. For example, and not by way of limitation, the relevant epitope may be comprised in an immunoglobulin molecule, for example, as set forth in U.S. patent application Ser. No. 08/363,276, by Bona et al., the contents of which is hereby incorporated in its entirety herein by reference. Alternatively, more than one epitope may be expressed within the same open reading frame.

Nucleic acids encoding the relevant epitope and optionally comprising elements that aid in its expression, stability, and/or immunogenicity may be comprised in a cloning vector such as a plasmid, which may be propagated using standard techniques to produce sufficient quantities of nucleic acid for immunization. The entire vector, which may preferably be a plasmid which is a mammalian expression vector comprising the cloned sequences, may be used to immunize the infant animal. Sequences encoding more than one epitope may be comprised in a single vector.

Examples of nucleic acids which may be used according to the invention are set forth in International Application Publication No. WO 94/21797, by Merck & Co. and Vical, Inc., and in International Application Publication No. WO 90/11092, by Vical, Inc., the contents of which are hereby incorporated in their entireties herein by reference.

Different species of nucleic acid, encoding more than one epitope of one or more target antigens, may be comprised in the same composition or may be concurrently administered as separate compositions.

The term "effective amount", as used herein, refers to an amount of nucleic acid encoding a relevant epitope of a target antigen, which, when introduced into a infant mammal, results in a substantial increase in the immune response of the mammal to the target antigen. Preferably, the cellular and/or humoral immune response to the target antigen is increased, following the application of methods of the invention, by at least four-fold, and preferably by at least between 10-fold and 100-fold (inclusive), above baseline. The immunity elicited by such genetic immunization may develop rapidly after the completion of the immunization (e.g., within 7 days), and may be long lasting (e.g., greater than 9 months). The need for "boosting" in order to achieve an effective immune response may be diminished by the present invention. In preferred embodiments, the effective amount of nucleic acid is introduced by multiple inoculations (see below).

In specific, nonlimiting embodiments of the invention, nucleic acid encoding between 1–500 picomoles of relevant epitope, preferably between 20–100 picomoles of relevant epitope, and more preferably between 40–100 picomoles of relevant epitope per gram weight of the infant mammal may be administered.

The nucleic acids of the invention may be comprised in a pharmaceutically acceptable carrier, for example, but not limited to, physiologic saline or liposomes. In specific, nonlimiting embodiments, the concentration of nucleic acid preferably ranges from 30–100 $\mu$g/100 $\mu$l. In certain embodiments, it may be desirable to formulate such compositions as suspensions or as liposomal formulations.

5.2. Methods of Immunization

The present invention provides for a method for immunizing an infant mammal against a target antigen, comprising inoculating the mammal with an effective amount of a nucleic acid encoding a relevant epitope of the target antigen in a pharmaceutically acceptable carrier.

The term "infant", as used herein, refers to a human or non-human mammal during the period of life following birth wherein the immune system has not yet fully matured. In humans, this period extends from birth to the age of about nine months, inclusive. In mice, this period extends from birth to about four weeks of age. The terms "newborn" and "neonate" refer to a subset of infant mammals, which have essentially just been born. Other characteristics associated with "infants" according to the invention include, an immune response which has: (i) susceptibility to high-zone tolerance (deletion/anergy of T cell precursors, increased tendency to apoptosis); (ii) a Th2 biased helper response (phenotypical particularities of neonatal T cells; decreased CD40L expression on neonatal T cells); (iii) reduced magnitude of the cellular response (reduced number of functional T cells; reduced antigen-pre-senting cell function); and (iv) reduced magnitude and restricted isotope of humoral response (predominance of IgM$^{high}$ IgD$^{low}$ B cells, reduced cooperation between Th and B cells).

In specific nonlimiting embodiments of the invention, nucleic acid immunization may be administered to an infant animal wherein maternal antibodies remain present in detectable amounts. In a related embodiment, the pregnant mother may be immunized with a nucleic acid-based vaccine prior to delivery so as to increase the level of maternal antibodies passively transferred to the fetus.

The terms "immunize" or "immunization" or related terms refer herein to conferring the ability to mount a substantial immune response (consisting of antibodies or cellular immunity such as effector CTL) against a target antigen or epitope. These terms do not require that completely protective immunity be created, but rather that a protective immune response be produced which is substantially greater than baseline. For example, a mammal may be considered to be immunized against a target antigen if the cellular and/or humoral immune response to the target antigen occurs following the application of methods of the invention. Preferably, immunization results in significant resistance to the disease caused or triggered by pathogens expressing target antigens.

The term "inoculating", as used herein, refers to introducing a composition comprising a nucleic acid according to the invention into a infant animal. Such introduction may be accomplished by any means and route known in the art, including intramuscular, subcutaneous, intravenous, intraperitoneal, intrathecal, oral, nasal, rectal, etc. administration. Preferably, inoculation is performed by intramuscular injection.

The effective amount of nucleic acid is preferably administered in several inoculations (that is to say, the effective amount may be split into several doses for inoculation). The number of inoculations is preferably at least one, and is more preferably three.

The success of the inoculations may be confirmed by collecting a peripheral blood sample from the subject between one and four weeks after immunization and testing for the presence of CTL activity and/or a humoral response directed against the target antigen, using standard immunologic techniques.

In specific, nonlimiting embodiments, the present invention may be used to immunize a human infant as follows. A human infant, at an age ranging from birth to about 9 months, preferably at an age ranging from birth to about 6 months, more preferably at an age ranging from birth to about 1 month, and most preferably at an age ranging from birth to about 1 week, may commence a program of injections whereby the infant may be injected intramuscularly three times at 3–7 day intervals with a composition comprising 1–100 manomoles of DNA encoding a relevant epitope of a target antigen, preferably at a DNA concentration of 1–5 mg/100 $\mu$l, wherein the target antigen may by a protein from a pathogen, for example respiratory syncytial virus, rotavirus, influenza virus, hepatitis virus, or HIV virus (see above).

Accordingly, the present invention provides for compositions for use in immunizing an infant mammal against a target antigen, comprising a nucleic acid encoding said target antigen in an amount effective in inducing a cellular (e.g. CTL) and/or humoral immune response.

It is believed that one of the advantages of the methods of the invention is that mammals immunized by such methods may exhibit a lesser tendency to develop an allergy or other adverse reaction after exposure to target antigens. Further, DNA vaccination of infants may reduce the risk of tolerance induction following other vaccination protocols which require successive administration of relatively high doses of antigen.

6. EXAMPLE: INDUCTION OF CELLULAR IMMUNITY AGAINST INFLUENZA VIRUS NUCLEOPROTEIN IN NEWBORN MICE BY GENETIC VACCINATION

6.1. Materials And Methods

Plasmids. The NPV1 plasmid (obtained from Dr. Peter Palese) was constructed by inserting a cDNA derived from the nucleoprotein gene of A/PR8/34 into the BglII site of a mutated pBR322 vector, namely pCMV-IE-AKi-DHFR (Whong et al., 1987, J. Virol. 61:1796), downstream from a 1.96 kb segment of the enhancer, promoter and intron A sequence of the initial early gene of cytomegalovirus and upstream of a 0.55 kb segment of the β globin polyadenylation signal sequence as described in Ulmer et al., 1993, Science 259:1745. The modified pBR322 vector without the NP sequence (termed the "V1 plasmid") was employed as a control. PRc/CMV-HA/WSN plasmid (pHA plasmid or WSN-HA plasmid) was constructed by inserting HA of A/WSN/33 (subtype H1N1) strain of influenza virus into the PRc/CMV mammalian expression vector and donated by Dr. Peter Palese (Mount Sinai School of Medicine). All plasmids were propagated in *Escherichia coli* and purified by the alkaline lysis method (Id.).

Viruses. The influenza virus strains A/PR8/34 (H1N1), A/HK/68(H3N2), A/Japan/305/57(H2N2) and B Lee/40 were grown in the allantoic cavity of embryonated hen eggs as described in Kilbourne, 1976, J. Infect. Dis. 134:384–394. The A/HK/68 virus adapted to mice was provided by Dr. Margaret Liu (Merck Research Laboratories). The influenza virus strain A/WSN/33 was grown in MDBK cells and purified from supernatants.

Immunization. One month old adult mice were vaccinated with 30 μg of NPV1, pHA or control plasmid dissolved in 100 μl of physiologic saline by injection into the anterior tibial muscle of the shaved right leg using a disposable 28 gauge insulin syringe that was permitted to penetrate to a depth of 2 mm; three injections with 30 μg DNA were carried out at three week intervals. Newborn mice were immunized with 30 μg of plasmid dissolved in 50 μl of physiologic saline by similar injection into the right gluteal muscle of Days 1, 3 and 6 after birth of life. Some newborn mice were injected intraperitoneally ("IP") on Day 1 after birth with PR8 or B Lee live virus (5 μg in 0.1 ml saline). One month after completion of the vaccination schedule, some mice were boosted with live virus in saline at a dose of $1 \times 10^3$ $TCID_{50}$ injected ip.

Infection. Mice were challenged via the aerosol route with $1.5 \times 10^4$ $TCID_{50}$ of A/PR8/34 (LD100) or $3.2 \times 10^5$ $TCID_{50}$ of A/HK/68 ($LD_{100}$ virus) or $3 \times 10^7$ $TCID_{50}$ of A/WSN/33 ($LD_{100}$). Exposure was carried out for 30 minutes in an aerosol chamber to which a nebulizer (Ace Glass, Inc.) was attached via a vacuum/pressure system pump operated at a rate of 35 L/min and a pressure of 15 lb/in$^2$. Mice were observed once daily post-infection and their survival was recorded.

Viral Lung Titers. Processing of lung tissue was carried out with at least three mice from each treatment group as described in as described in Isobe et al., 1994, Viral Immunol. 7:25–30, and viral titers in lung homogenates were determined using an MDCK cell-chicken RBC hemagglutination assay.

Cytotoxic Assay. A primary cytotoxicity assay was carried out by incubating effector cells with $5 \times 10^3$ $^{51}$Cr-labeled target cells at different effector-to-target ratios in 96-well V-bottom plates. P815 target cells were infected with PR8 virus for 1 hour before labeling with $^{51}$Cr or incubated during the assay with 5–10 μg/ml of $NP_{147-155}$. After incubation for 4 hours at 37° C. in 5% $CO_2$, the supernatant was harvested and radioactivity released was determined using a gamma counter. A secondary cytotoxicity assessment was carried out after co-culturing equal numbers of lymphocytes from test animals and x-irradiated, virus-infected or $NP_{147-155}$-coated lymphocytes from non-immunized BALB/c mice for five days in RPMI supplemented with fetal calf serum ("FCS") 10% and 50 μM 2-mercaptoethanol; the secondary CTL assay itself was conducted using the $^{51}$Cr release assay described above, and the results were expressed as the percentage of specific lysis determined in triplicate for each effector:target ratio employed, as follows:

$$100(\text{actual}-\text{spontaneous release}) \div (\text{maximum}-\text{spontaneous release}-\text{background release}) \pm SD$$

Limiting Dilution Analysis of CTL Precursors. The number of antigen-specific CTL precursors in the spleens of immunized mice were assessed by incubating single-cell suspensions of splenic responder cells in six steps of two-fold dilutions with $2.5 \times 10^5$ X-irradiated, PR8-infected syngeneic splenocytes. After five days in complete RPMI medium, individual microtiter cultures were assayed using $^{51}$Cr release from P815 cells infected with influenza virus; uninfected P815 cells were used as a control. Those wells exhibiting $^{51}$Cr release greater than background plus three standard deviations were regarded as positive. The percentage of cultures in one dilution step regarded as negative for specific cytotoxicity were plotted logarithmically against the number of responder cells/well, and the frequency of CTL precursors was determined by linear regression analysis using the following formula:

$$-\ln(\text{negative-well index}) \div (\text{number of responder cells/well}) = 1/(\text{number of responder cells/well at 0.37 negative well index}).$$

The number of precursor cells is represented as 1/frequency for purposes of comparison.

Plasmid Detection by PCR. Injected and control muscle tissue was removed one month after completion of the vaccination schedule, immediately frozen in ethanol-dry ice, and stored at −80° C. Frozen tissue was homogenized in lysis buffer and DNA was extracted as described in Montgomery, 1993, DNA and Cell Biol. 12:777–783 and Ulmer et al., 1993, Science 254:1745. A forty-cycle PCR reaction was carried out with NP-specific primers located at the following nucleotide positions: 1120 (minus strand; 5'-[CATTGTCTAGAATTTGAACTCCTCTAGTGG]-3'; SEQ ID NO:18; Cerbone) as well as 468 (positive strand; 5'-[AATTTGAATGATGCAAC]-3'; SEQ ID NO:20). A PCR product with a specific signal of 682 bp was visualized using ethidium bromide stained agarose gels.

Hemagglutination Inhibition Assay. Sera from immunized mice were treated with receptor destroying enzyme (RDE/neuraminidase) for 1 hour at 37° C. in a waterbath. Two-fold serial dilutions of RDE-treated sera were incubated with 0.5% human erythrocyte saline suspension in the presence of hemagglutinating titers of influenza virus. The experiment was carried out in triplicate wells. After 45 minutes incubation in a 96-well round bottom RIA plates (Falcon) at room temperature, the results were read and expressed as $\log_2$ of the last inhibitory dilution. Negative controls (blank sera) and positive controls (HA specific monoclonal antibodies) were included in the experiment.

Cytokine Measurement by ELISA. T cells were incubated, for four days, with antigen and irradiated accessory cells, and then 100 microliters of supernatant were harvested from each microculture. The concentrations of IFN gamma and IL-4 were measured using ELISA test kits (Cytoscreen, from Biosource Int. and Interest from Genzyme, respectively). Standards with known concentrations were included in the assay. The optical densities were assessed at 450 nm absorbance after blanking the ELISA read on the null concentration wells.

6.2. Results

Priming of CTL Precursors via Neonatal DNA Vaccination. The optimal schedule for DNA vaccination in the experiments described was developed in pilot studies. Newborn mice were immunized with 30 μg of NPV1 or control plasmid on Days 1, 3 and 6 after birth; adult animals were vaccinated with the same amount of DNA immunogen on Days 0, 21 and 42 of the study. One month after the completion of this standard series of vaccinations, certain test animals were boosted with live PR8 virus.

The lymphocytes, directly isolated from newborn and adult mice vaccinated with NPV1 and boosted with PR8 virus, lysed target cells coated in vitro with $NP_{147-155}$, which is recognized by CTL in association with $K^d$ MHC-molecules of Class I (FIGS. 1A–F). No primary cytotoxicity was observed in vitro with lymphocytes from newborns immunized on Day 1 with PR8 virus and boosted one month later with PR8 virus. As expected, significant cytotoxicity was observed after in vitro expansion of splenocytes from mice immunized with NP-V1 plasmid or PR8 virus only. No significant cytotoxicity was observed in the case of mice immunized with control virus or B/Lee virus. These data clearly indicate that vaccination with NPV1 with or without subsequent boosting with native virus induced an expansion of NP-specific CTL precursors in both newborn animals and adults; however, both primary cytotoxicity and immunologically significant secondary cytotoxicity were observed only in animals fully immunized with NPV1 and boosted with virus.

Frequency of NP-specific CTL Precursors. An immunologically significant increase in the frequency of NP-specific CTL precursors was observed in animals immunized with NPV1 and boosted with PR8 virus, accounting for the presence of primary cytotoxicity in this particular group (FIGS. 2A–B). The increased frequency of specific precursors is presumably due to sustained biosynthesis of NP antigen, which primed and expanded this population of NP-specific lymphocytes. Plasmid was detected by qualitative PCR one month after completion of the immunization series in gluteal muscle, the site of injection of NPV1 in newborns, and in tibial muscle, the site of injection of NPV1 in adult animals (FIG. 3).

Induction of Cross-reactive CTLs via DNA Immunization. The induction of cross-reactive CTLs against NP-subtypes in adult animals immunized with type A influenza virus is well-characterized and understood to be related to the limited genetic variation of NP compared to hemagglutinin (HA) and neuraminidase (NA), which are viral surface proteins. In a similar manner, CTLs derived from newborn mice immunized with NPV1 and boosted with PR8 virus exhibited increased lysis of P815 cells infected with a variety of influenza strains, including PR8($H_1N_1$), A/HK/68 ($H_3N_2$) and A/Japan($H_2N_2$) viruses, but not the Type B virus B/Lee, after in vitro stimulation with PR8 virus infected cells or $NP_{147-155}$ peptide (FIGS. 4A–C).

Effect of DNA Immunization on Pulmonary Virus Titer. The increased activity of CTLs in those animals vaccinated with NPV1 is correlated with decreased viral titers in lung tissue measured after aerosol challenge with one $LD_{100}$ of PR8 or HK viruses. Although no difference in viral titers was observed in mice immunized with NPV1 or control plasmid three days after PR8 challenge, a statistically significant reduction was observed in both newborn ($p<0.05$) and adult mice ($p<0.025$; Table I) seven days after challenge. No virus was detected in the lungs of mice that survived challenge for more than 16 days. It is important to note that decreased viral titers in lung tissue were observed in mice challenged with PR8 virus one or three months after completing the immunization ($p<0.05$).

Effect of DNA Immunization on Clinical Course of Infection and Survival. Genetic immunization of adult mice with NPV1 induced protective immunity in 80% of animals challenged with PR8 virus one month after the last immunization ($p<0.01$; FIGS. 5A–D) and in 57 percent of adult animals challenged three months after the last immunization ($p<0.05$; FIG. 5E). An increased survival after challenge was observed in three month old mice immunized with NPV1 as newborns, indicating that during the three month period a more vigorous expansion of CTL precursors was elicited after genetic immunization ($p<0.02$, FIG. 5B). Only 10% of adult animals challenged with HK virus survived (FIGS. 5A–D), findings that differ from those previously reported (Ulmer et al., 1993, Science 259:1745–1749) even though the DNA immunogen and HK strain used in challenge were identical. The relative decrease in survival we observed could be explained by the intranasal route of challenge used previously (Id.), which is less likely to provide productive infection of the lower as well as upper respiratory tract compared to the aerosol challenge employed in these studies. Despite their immunoresponsiveness, one-month old mice immunized with NPV1 as newborns exhibited reduced survival after challenge with PR8 and no survival after challenge with HK virus compared to immunized adults and three month old mice infected with NPV1 as newborns, which exhibited significant survival after challenge with LD100 of PR8 virus.

The pneumonia that occurs after influenza infection is accompanied by weight loss in these animals. Adult mice treated with control plasmid and challenged with a lethal dose of PR8 gradually lost weight until they expired (Days 7–9), while the surviving animals immunized with NPV1 recovered their prechallenge body weight by Day 10 after significant initial weight loss post-challenge (Day 2–7; FIGS. 6A–B). Similar results were obtained with one-month old mice which had been immunized after birth as newborns with NPV1 (FIGS. 6A–B) or with three month old mice.

Effect of DNA Immunization with a Plasmid Which Encodes HA of Influenza Virus (pHA plasmid). Immunization of newborn mice with pHA according to the same protocol as NPV1 was followed by specific antibody production as early as 1 month after birth which persisted at least three months after birth (Table 2). These antibodies displayed hemagglutination inhibiting properties, like antibodies obtained by live-virus or plasmid immunization of adult mice. In consequence, immunization of neonates with pHA elicited protective, virus-specific antibodies.

Immunization of mice with pHA primed T helper cells which were then able to secrete cytokines upon in vitro restimulation with virus (Table 3). Whereas pHA injection of adult mice elicited predominantly TH1 type cells, inoculation of neonates with the same plasmid lead to the development of a mixed Th1/Th2 response. DNA immunization of neonates as well as adult mice with pHA conferred significant protection to lethal challenge ($LD_{100}$) with WSN or PR8 virus as early as one month after immunization (FIGS. 7A–D).

6.3. Discussion

Numerous studies have indicated that the genetic immunization of adult mice, chickens, ferrets and monkeys with cDNAs containing NP or HA sequences of various strains of type A influenza virus can induce protective cellular and humoral immunity (Ulmer et al., 1993, Science 258:1745–1749; Montgomery et al., 1993, DNA and Cell Biol. 12:777–783; Fyneu et al., 1993, Proc. Natl. Acad. Sci. U.S.A. 90:11478–11482; Justevicz et al., 1995, J. Virol. 19:7712–7717; Donnely et al., 1995, Nature Med. 1:583–587). The results presented herein are the first evidence that such immunization has a comparable effect in newborn animals, and that cellular immunity is generated consequent to a strong priming effect characterized by a significant increase in the frequency of antigen-specific CTL precursors. The survival after challenge, the reduction in viral lung titers and recovery of prechallenge body weight compared to controls in animals that were vaccinated with NPV1 or pHA is indicative of effective secondary immune responses.

Previous studies in adult mice have indicated that immunization with homologous virus affords 100% protection to lethal challenge, while only 50–60% protection occurs in normal mice infused with NP-specific T cell clones (Taylor et al., 1986, Immunology 58:417–420) or in PR8-immunized B cell deficient ($J_HD-/-$) animals (Bot et al., 1996, J. Viroo. 70:5668–5672), indicating that effective protection requires both humoral and cellular responsiveness, the former presumably mitigating the spread of virus and the extent of pulmonary lesions. The absence of a protective antibody response in the studies carried out with NPV1 plasmid as well as slow expansion of CTL precursors during the first month of life may explain the relatively poor survival of one month old mice that were immunized with NPV1 plasmid as newborns. The increased survival of three month old mice immunized as newborns with NPV1 plasmid suggests that the expansion of CTL precursors continues after neonatal immunization, enabling the mice to develop a stronger cellular response when they become adults.

Further data indicates that the plasmid expressing the HA gene of WSN virus, injected after birth, elicits both humoral and cellular responses mirrored in an increased survival. For example, neonatal immunization with pHA triggered an antibody response associated with a helper response which conferred significant protection upon later challenge with influenza virus.

TABLE 1

Effect of immunization with NPV1 plasmid on pulmonary virus titer measured after challenge with lethal doses of PR8 or HK virus.

| age of animals | immunization | challenge with $1.5 \times 10^4$ $TCID_{50}$ PR8 virus | | | challenge with $3.2 \times 10^5$ $TCID_{50}$ HK virus | | |
|---|---|---|---|---|---|---|---|
| | | 3 d | 7 d | 16 d | 3 d | 7 d | 16 d |
| adult | nil | 4.6 ± 0.5 | 3.8 ± 0.1 | +[3] | 6.4 ± 0.7 | 5.7 ± 0.3 | + |
| | PR8 virus | 0 | 0 | ND | 5.7 ± 0.3 | 0 | ND |
| | control plasmid | 4.8 ± 0.1 | 3.7 ± 0.5 | + | 6.8 ± 0.1 | 5.7 | + |
| | NPV1-1 month[1] | 4.0 ± 0.3 | 0.9 ± 1.5 | 0[4] | 5.8 ± 0.1 | 0.6 ± 1.1 | 0 |
| | NPV1-3 months[2] | 4.8 ± 0.1 | 0.2 ± 0.2 | 0 | 6.9 ± 0.7 | 4.6 ± 0.8 | + |
| newborn | control plasmid | 5.9 ± 0 | 4.6 ± 0.2 | + | ND | ND | ND |
| | NPV1-1 month | 4.5 ± 1.2 | 1.2 ± 2.1 | 0 | 6.6 ± 0.3 | 5.1 ± 0.6 | + |
| | NPV1-3 months | 4.1 ± 0.5 | 0.9 ± 1.2 | 0 | ND | ND | ND |

Mice were sacrificed 1 month after the last immunization. Data are expressed as $log_{10}$ of viral titer in $TCID_{50}$ units.
ND—not done
[1]mice challenged 1 month after completing the immunization
[2]mice challenged 3 months after completing the immunization
[3]no survivors at day 16 after challenge
[4]pulmonary virus titer in mice which survived more than 16 days

TABLE 2

HI titer of BALB/c mice immunized with WSN virus or plasmids

| Mice immunized as: | Immunization with: | No. of mice: | Prebleeding titer WSN | Prebleeding titer PR8 | Time of bleeding: | Titer against: WSN | Titer against: PR8 | No. of responders WSN | No. of responders PR8 | Boost: | Titer 7 days after boost against: WSN | Titer 7 days after boost against: PR8 |
|---|---|---|---|---|---|---|---|---|---|---|---|---|
| Adults | WSN | 5 | 0[a] | 0 | 1 mo | 8.2 ± 1.1[b] | 1.2 ± 0.8 | 5/5 | 5/5 | WSN | 8.2 ± 1.3 | 2.2 ± 1.6 |
|  | CP | 3 | 0 | 0 | 1 mo | 0 | 1.0 ± 0.7 | 0/3 | 1/3 | — | 0 | 0 |
|  | CP | 3 | 0 | 0 | 1 mo | 0 | 0 | 0/3 | 0/3 | WSN | 7.3 ± 5.3 | 1.3 ± 2.3 |
|  | pHA | 16 | 0 | 0 | 1 mo | 5.5 ± 3.4 | 0 | 12/16 | 0/16 | WSN | 8.3 ± 1.5 | 1.0 ± 1.9 |
|  | pHA | 8 | 0 | 0 | 3 mo | 8.7 ± 3.8 | 0 | 5/8 | 0/8 | WSN | 8.3 ± 1.5 | 2.0 ± 2.0 |
|  | pHA | 9 | 0 | 0 | 6 mo | 1.0 ± 0 | 0 | 2/9 | 0/9 | WSN | 8.3 ± 0.6 | 1.3 ± 0.6 |
|  | pHA | 3 | 0 | 0 | 9 mo | 0 | 0 | 0/3 | 0/3 | WSN | 5.6 ± 0.6 | 5.0 ± 1.7 |
| Newborns | CP | 5 | ND | ND | 1 mo | 0 | 0 | 0/5 | 0/5 | WSN | 7.0 ± 0.8 | 0 |
|  | pHA | 19 | ND | ND | 1 mo | 5.2 ± 2.7 | 0 | 12/19 | 0/19 | WSN | 9.4 ± 0.9 | 2.0 ± 1.6 |
|  | pHA | 4 | ND | ND | 3 mo | 3.3 ± 1.5 | 0 | 3/4 | 0/4 | WSN | 8.8 ± 2.9 | 3.2 ± 2.5 |

[a] 0 = <1:40
[b] $\log_2$ dilution
ND—not done

TABLE 3

Table Lymphokine production by T cells from mice immunized with pHA plasmid or WSN virus:

| Group Immunization | Boost | Lymphkines | Adult mice nil* | Adult mice WSN* | Newborn mice nil | Newborn mice WSN |
|---|---|---|---|---|---|---|
| nil | — | IFNγ | 0 | 0 | ND | ND |
|  | — | IL-4 | 0 | 0 | ND | ND |
| CP | — | IFNγ | 0 | 11 ± 5** | 14 ± 5 | 22 ± 3 |
|  | — | IL-4 | 0 | 0 | 0 | 0 |
|  | WSN | IFNγ | 24 ± 1 | 158 ± 4 | 89 ± 28 | 261 ± 26 |
|  | WSN | IL-4 | 236 ± 11 | 79 ± 19 | 198 ± 5 | 141 ± 39 |
| pHA | — | IFNγ | 9 ± 1 | 60 ± 2 | 0 | 29 ± 18 |
|  | — | IL-4 | 0 | 0 | 2 ± 2 | 6 ± 3 |
|  | WSN | IFNγ | 19 ± 3 | 284 ± 10 | 38 ± 8 | 179 ± 50 |
|  | WSN | IL-4 | 54 ± 3 | 31 ± 4 | 138 ± 4 | 257 ± 24 |
| WSN | — | IFNγ | 52 ± 2 | 214 ± 11 | 103 ± 30 | 51 ± 8 |
|  | — | IL-4 | 48 ± 3 | 181 ± 3 | 132 ± 6 | 248 ± 20 |
|  | WSN | IFNγ | 10 ± 1 | 127 ± 3 | 9 ± 5 | 61 ± 12 |
|  | WSN | IL-4 | 218 ± 4 | 235 ± 12 | 228 ± 8 | 594 ± 5 |

*$1.5 \times 10^5$ nylon wool non-adherent splenocytes were incubated for four days with $1.5 \times 10^5$ irradiated BALB/c splenocytes with or without 10 μg/ml UV-innactivated WSN virus, in presence of 1 U/ml exogenous IL-2.
**concentration of cytokines in supernatant was determined by ELISA and expressed as pg/ml. Values below background ± 3 × SD were considered 0.

Various publications are cited herein, the contents of which are incorporated by reference in their entireties.

What is claimed is:

1. A method for immunizing an infant mammal against a target viral antigen, comprising inoculating the mammal, while an infant, with an effective amount of a naked recombinant nucleic acid molecule encoding a peptide comprising one or more relevant epitopes of the target viral antigen in a pharmaceutical carrier, such that a therapeutically effective amount of the relevant peptide is expressed in the infant mammal, wherein said infant is immunized.

2. The method of claim 1, wherein the target antigen is a respiratory syncytial virus antigen.

3. The method of claim 1, wherein the target antigen is a rotavirus antigen.

4. The method of claim 1, wherein the target antigen is a measles virus antigen.

5. The method of claim 1, wherein the target antigen is a human immunodeficiency virus antigen.

6. The method of claim 1, wherein the target antigen is a hepatitis virus antigen.

7. The method of claim 1, wherein the target antigen is a hepatitis B virus antigen.

8. The method of claim 1, wherein the target antigen is a herpes simplex virus antigen.

9. The method of claim 1, wherein the target antigen is an influenza virus antigen.

10. The method of claim 1 wherein maternal antibodies are present in detectable amounts in the infant mammal.

11. The method of claim 1 wherein the mammal is a human having an age extending from birth to the age of nine months.

12. The method of claim 1 wherein the mammal is a human having an age extending from birth to the age of one month.

13. The method of claim 1 wherein the infant mammal is a neonate.

14. A method for immunizing an infant mammal against a target viral antigen, comprising injection into the mammal of an effective amount of a naked nucleic acid molecule encoding a viral peptide comprising the target antigen comprising one or more relevant viral epitopes in a pharmaceutically acceptable carrier, such that a therapeutically effective amount of the relevant peptide is expressed in the infant mammal, wherein said infant is immunized.

15. A method for immunizing an infant mammal against a target viral antigen, comprising inoculating the mammal with a therapeutically effective amount of a naked recombinant nucleic acid molecule encoding a peptide comprising one or more relevant viral epitopes of the target viral antigen in a pharmaceutical acceptable carrier, wherein; (i) the therapeutical effective amount of nucleic acid is introduced by a plurality of inoculations all administered while the animal is an infant; and (ii) immunization results in significant resistance to a disease associated with a pathogen that expresses the target antigen.

16. The method of claim 15, wherein the mammal is a human.

17. The method of claim 15, wherein the mammal is a human and the first of the plurality of injections is administered at an age extending form birth to about six months.

18. The method of claim 15, wherein the mammal is a human and the first of the plurality of injections is administered at an age extending from birth to about one month.

19. The method of claim 15, wherein the mammal is a human and the first of the plurality of injections is administered at an age extending from birth to about one week.

* * * * *